US007220723B2

(12) United States Patent
Tracey et al.

(10) Patent No.: US 7,220,723 B2
(45) Date of Patent: May 22, 2007

(54) INHIBITORS OF THE INTERACTION BETWEEN HMGB POLYPEPTIDES AND TOLL-LIKE RECEPTOR 2 AS ANTI-INFLAMMATORY AGENTS

(75) Inventors: Kevin J. Tracey, Old Greenwich, CT (US); Huan Yang, Douglaston, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 168 days.

(21) Appl. No.: 10/456,947

(22) Filed: Jun. 6, 2003

(65) Prior Publication Data
US 2004/0053841 A1 Mar. 18, 2004

(51) Int. Cl.
A61K 38/00 (2006.01)
A61K 49/00 (2006.01)
(52) U.S. Cl. .................. 514/12; 514/2; 530/350; 435/7.1; 435/325; 424/9.1
(58) Field of Classification Search ............ 514/12, 514/2; 530/350; 435/7.1, 325; 424/9.1
See application file for complete search history.

(56) References Cited

U.S. PATENT DOCUMENTS

| 5,594,114 | A | 1/1997 | Goodearl et al. |
| 6,303,321 | B1 | 10/2001 | Tracey et al. |
| 6,448,223 | B1 | 9/2002 | Tracey et al. |
| 6,468,533 | B1 | 10/2002 | Tracey et al. |
| 2003/0027260 | A1 | 2/2003 | Goddard et al. |
| 2003/0032090 | A1 | 2/2003 | Hardiman et al. |
| 2003/0032674 | A1 | 2/2003 | Hwang |
| 2003/0060410 | A1 | 3/2003 | Tracey et al. |
| 2003/0144201 | A1 | 7/2003 | Tracey et al. |
| 2004/0005316 | A1 | 1/2004 | Tracey et al. |

FOREIGN PATENT DOCUMENTS

| JP | 10082788 | 3/1998 |
| WO | WO 98/50547 | 11/1998 |
| WO | WO 99/20756 A2 | 4/1999 |
| WO | WO 99/20756 A3 | 4/1999 |
| WO | WO 99/59609 | 11/1999 |
| WO | WO 00/47104 | 8/2000 |
| WO | WO 00/75358 A2 | 12/2000 |
| WO | WO 01/72993 A1 | 4/2001 |
| WO | WO 01/36488 A1 | 5/2001 |
| WO | WO 01/55386 A1 | 8/2001 |
| WO | WO 01/75067 A2 | 10/2001 |
| WO | WO 01/90151 A2 | 11/2001 |
| WO | WO 01/90151 A3 | 11/2001 |
| WO | WO 02/074337 A1 | 9/2002 |
| WO | WO 02/089743 A2 | 11/2002 |
| WO | WO 02/090520 A2 | 11/2002 |
| WO | WO 02/090520 A3 | 11/2002 |
| WO | WO 02/092004 A2 | 11/2002 |
| WO | WO 03/022296 A1 | 3/2003 |

OTHER PUBLICATIONS

Kim, J., et al., "Activation of Toll-Like Receptor 2 in Acne Triggers Inflammatory Cytokine Responses," J. Immunol., 169(3):1535-1541 (2002).
Matsuguchi, T., et al., "Gene Expression of Toll-Like Receptor 2, But Not Toll-Like Receptor 4, Is Induced by LPS and Inflammatory Cytokines in Mouse Macrophages," J. Immunol., 165(10): 5767-5772 (2000).
Jones, B. W., et al., "Different Toll-Like Receptor Agonists Induce Distinct Macrophage Responses," J. Leukoc. Biol., 69(6):1036-1044 (2001).
Means, T. K., et al., "Human Toll-Like Receptors Mediate Cellular Activation by Mycobacterium tuberculosis," J. Immunol., 3920-3927 (1999).
Abraham, E., et al., "Cutting Edge: HMG-1 as a Mediator of Acute Lung Inflammation," J. Immunol., 165:2950-2954 (2000).
Andersson, U., et al., "High Mobility Group 1 Protein (HMG-1) Stimulates Proinflammatory Cytokine Synthesis in Human Monocytes," J. Exp. Med., 192(4):565-570 (2000).
Bustin, M. "Revised Nomenclature for High Mobility Group (HMG) Chromosomal Proteins," Trends Biochem. Sci., 26(3):152-153 (2001).
Degryse, B., et al., "The High Mobility Group (HMG) Boxes of the Nuclear Protein HMG1 Induce Chemotaxis and Cytoskeleton Reorganization in Rat Smooth Muscle Cells," J. Cell Biol., 152(6):1197-1206 (2001).
Wang, H., et al., "HMG-1 as a Late Mediator of Endotoxin Lethality in Mice," Science, 285:248-251 (1999).
Wang, H., et al., "Proinflammatory Cytokines (Tumor Necrosis Factor and Interleukin 1) Stimulate Release of High Mobility Group Protein-1 by Pituicytes," Surgery, 126:389-392 (1999).
Bianchi, M. E., et al., "The DNA Binding Site of HMG1 Protein Is Composed of Two Similar Segments (HMG Boxes), Both of Which Have Counterparts in Other Eukaryotic Regulatory Proteins," EMBO J., 11(3): 1055-1063 (1992).
Aderem, A. and Ulevitch, R.J., "Toll-Like Receptors in the Induction of the Innate Immune Response," Nature, 406:782-787 (2000).
Beutler, E., et al., "Synergy Between TLR2 and TLR4: A Safety Mechanism," Blood Cells, Mol. Dis., 27(4):728-730 (2001).

(Continued)

Primary Examiner—Chih-Min Kam
(74) Attorney, Agent, or Firm—Hamilton, Brook, Smith & Reynolds, P.C.

(57) ABSTRACT

The invention features a method of treating an inflammatory condition in an individual, comprising administering an agent that inhibits the interaction between a Toll-like receptor 2 (TLR2) and a high mobility group B (HMGB) polypeptide to the individual. The invention also features methods for identifying agents that inhibit the interaction between TLR2 and HMGB.

4 Claims, 13 Drawing Sheets

OTHER PUBLICATIONS

Iwaki, D., et al., "The Extracellular Toll-Like Receptor 2 Domain Directly Binds Peptidoglycan Derived from *Staphylococcus aureus*," *J. Biol. Chem.*, 277(27):24315-24320 (2002).

Kirschning, C.J., et al., Human Toll-Like Receptor 2 Confers Responsiveness to Bacterial Lipopolysaccharide, *J. Exp. Med.*, 188(11):2091-2097 (1998).

Li, M., et al., "An Essential Role of the NF-xB/Toll-Like Receptor Pathway in Induction of Inflammatory and Tissue-Repair Gene Expression by Necrotic Cells," *J. Immunol.*, 166:7128-7135 (2001).

Martin, M., et al., "Role of Innate Immune Factors in the Adjuvant Activity of Monophosphoryl Lipid A," *Infect. Immun.*, 71(5):2498-2507 (2003).

Opal, S.M. and Huber, C.E., "Bench-To-Bedside Review: Toll-Like Receptors and Their Role in Septic Shock," *Crit. Care*, 6(2):125-136 (2002).

Riedemann, N.C., et al., "Novel Strategies for the Treatment of Sepsis," *Nature Med.*, 9(5):517-524 (2003).

Scaffidi, P., et al., "Release of Chromatin Protein HMGB1 by Necrotic Cells Triggers Inflammation," *Nature*, 418:191-195 (2002).

Yang, R-B., et al., "Signaling Events Induced by Lipopolysaccharide-Activated Toll-Like Receptor 2," *J. Immunol.*, 163:639-643 (1999).

Yang, R-B., et al., "Toll-Like Receptor-2 Mediates Lipopolysaccharide-Induced Cellular Signalling," *Nature*, 395:284-288 (1998).

Zuany-Amorim, C., et al., "Toll-Like Receptors as Potential Therapeutic Targets for Multiple Diseases," *Nat. Rev. Drug Discov.*, 1:797-807 (2002).

Falciola, L., et al., "High Mobility Group 1 Protein is not Stably Associated with the Chromosomes of Somatic Cells," *J Cell Biol.* 137(1):19-26 (1997).

Sparatore, B., et al., "Extracellular High-Mobility Group 1 Protein is Essential for Murine Erythroleukaemia Cell Differentiation," *Biochem. J.* 320:253-256 (1996).

Freeman, B. D., et al., "The Role of Inflammation in Sepsis and Septic Shock: A Meta-Analysis of Both Clinical and Preclinical Trials of Anti-Inflammatory Therapies." in *Inflammation: Basis Principals and Clinical Correlates* (John I. Gallin and Ralph Snyderman eds., Lippincott, Williams & Wilkins, Philadelphia, 3rd ed. 1999), pp. 965-975.

Abaza, M.-S. I. and Atassi, M. Z., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *J Protein Chem.* 11(5):433-444 (1992).

Lederman, S., et al., "A Single Amino Acid Substitution in a Common African Allele of the CD4 Molecule Ablates Binding of the Monoclonal Antibody, OKT4," *Mol Immunol.* 28(11):1171-1181 (1991).

Colman, P.M., "Effects of Amino Acid Sequence Changes on Antibody-Antigen Interactions," *Res. Immunol.* 145(1):33-36 (1994).

Imamura, T., et al., "Interaction with p53 Enhances Binding of Cisplatin-Modified DNA by High Mobility Group 1 Protein," *J. Biol. Chem.*, 276(10):7534-7540 (2001).

Tsuda, K., et al., "Primary Structure of Non-Histone Protein HMG1 Revealed by the Nucleotide Sequence," *Biochemistry*, 27:6159-6163 (1988).

Meng, G., et al., "Antagonistic antibody prevents toll-like receptor 2-driven lethal shock-like syndromes," *J. Clin. Invest.*, 113(1):1473-1481 (2004).

Patel, M., et al., "TLR2 Agonist Ameliorates Established Allergic Airway Inflammation by Promoting Th1 Response and Not via Regulatory T Cells[1]," *J. Immunol*, 174:7558-7563 (2005).

Meng, G., et al., "Murine TLR2 expression anaylsis and systemic antagonism by usage of specific monoclonal antibodies," *Immunology Letters*, 98:200-207, (2005).

Yakushijin, T., et al., "Reduced expression and functional impairment of Toll-like receptor 2 on dendritic cells in chronic hepatitis C virus infection," *Hepatology Research*, 34:156-162 (2006).

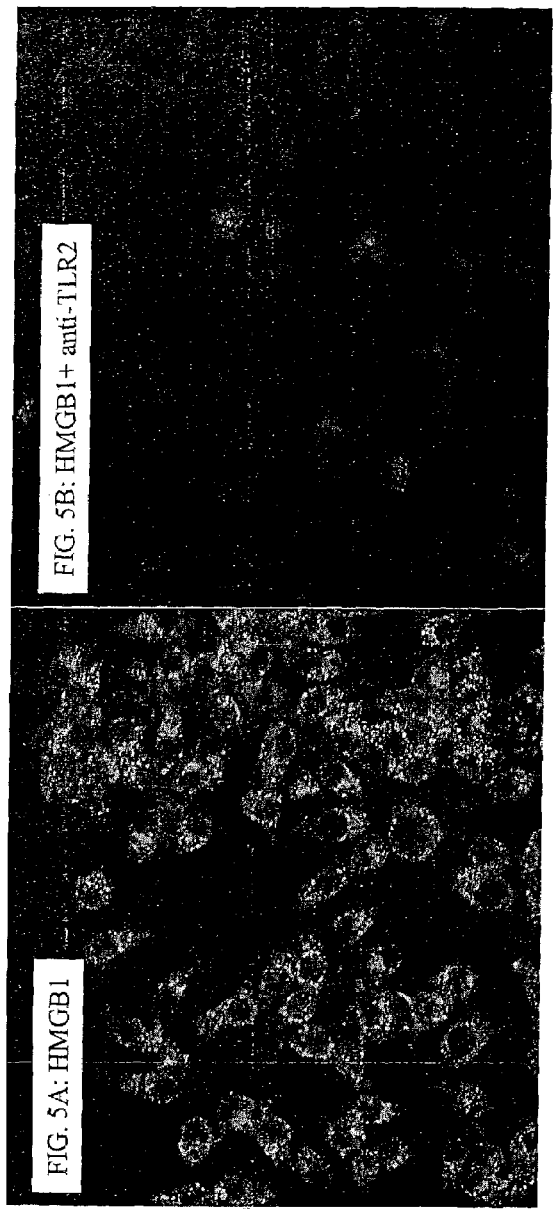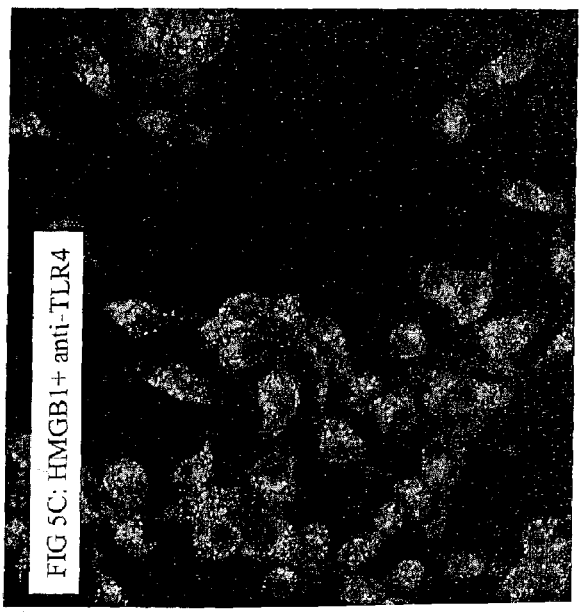

FIG. 6A     SEQ ID NO:1 - Human HMG1 amino acid sequence
1 mgkgdpkkpr gkmssyaffv qtcreehkkk hpdasvnfse fskkcserwk tmsakckgkf
61 edmakadkar yeremktyip pkgetkkkfk dpnapkrpps afflfcseyr pkikgehpgl
121 sigdvakklg emwnntaadd kqpyekkaak lkekyckdia ayrakgkpda akkgvvkaek
181 skkkkcceed ccdeedecee edeededeee dddde FIG. 6B     SEQ ID NO:2 - Mouse and Rat HMG1 amino acid sequence
1 mgkgdpkkpr gkmssyaffv qtcreehkkk hpdasvnfse fskkcserwk tmsakckgkf
61 edmakadkar yeremktyip pkgctkkkfk dpnapkrpps afflfcseyr pkikgehpgl
121 sigdvakklg emwnntaadd kqpyekkaak lkekyekdia ayrakgkpda akkgvvkaek
181 skkkkeeedd eedeedeeee eeeededeee dddde FIG. 6C     SEQ ID NO:3 - HUMAN HMG2 amino acid sequence
1 mgkgdpnkpr gkmssyaffv qtcreehkkk hpdssvnfac fskkcserwk tmsakekskf
61 edmaksdkar ydrcmknyvp pkgdkkgkkk dpnapkrpps afflfcsehr pkiksehpgl
121 sigdtakklg emwseqsakd kqpyeqkaak lkekyekdia ayrakgksea gkkgpgrptg
181 skkknepede eeeeeeded eeeededee FIG. 6D     SEQ ID NO:4 - Human, mouse and rat HMG1 A box protein sequence
1 pdasvnfsef skkcserwkt msakckgkfe dmakadkary eremktyipp kget FIG. 6E     SEQ ID NO:5 - Human, mouse and rat HMG1 B box protein sequence
1 napkrppsaf flfcseyrpk ikgehpglsi gdvakklgem wnntaaddkq pyekkaaklk
61 ekyekdiaa FIG. 7A
NG_000897 DNA (bases 658-1305)
ATGGGCAAAG GAGATCCTAA GAAGCCGACA GGCAAAATGT CATCATATGC
ATTTTTTGTG CAAACTTGTC GGGAGGAGCA TAAGAAGAAG CACCCAGATG
CTTCAGTCAA CTTCTCAGAG TTTTCTAAGA AGTGCTCAGA GAGGTGGAAG
ACCATGTCTG CTAAAGAGAA AGGAAAATTT GAAGATATGG CAAAGGCGGA
CAAGGCCCGT TATGAAAGAG AAATGAAAAC CTATATCCCT CCCAAAGGGG
AGACAAAAAA GAAGTTCAAG GATCCCAATG CACCCAAGAG GCTTCCTTCG
GCCTTCTTCC TCTTCTGCTC TGAGTATCGC CCAAAAATCA AGGAGAACA
TCCTGGCCTG TCCATTGGTG ATGTTGCGAA GAAACTGGGA GAGATGTGGA
ATAACACTGC TGCAGATGAC AAGCAGCCTT ATGAAAAGAA GGCTGCGAAG
CTGAAGGAAA AATACGAAAA GGATATAGCT GCATATCGAG CTAAAGGAAA
GCCTGATGCA GCAAAAAAGG GAGTTGTCAA GGCTGAAAAA AGCAAGAAAA
AGAAGGAAGA GGAGGAAGAT GAGGAAGATG AAGAGGATGA GGAGGAGGAG
GAAGATGAAG AAGATGAAGA AGATGAAGAA GAAGATGATG ATGATGAA FIG. 7B
NG_000897 Protein
MGKGDPKKPT GKMSSYAFFV QTCREEHKKK HPDASVNFSE FSKKCSERWK
TMSAKEKGKF EDMAKADKAR YEREMKTYIP PKGETKKKFK DPNAPKRLPS
AFFLFCSEYR PKIKGEHPGL SIGDVAKKLG EMWNNTAADD KQPYEKKAAK
LKEKYEKDIA AYRAKGKPDA AKKGVVKAEK SKKKKEEEED EEDEEDEEEE
EDEEDEEDEE EDDDDE FIG. 7C
AF076674 DNA (bases 1-633)
ATGGGCAAAG GAGATCCTAA GAAGCCGAGA GGCAAAATGT CATCATATGC
ATTTTTTGTG CAAACTTGTC GGGAGGAGCA TAAGAAGAAG CACTCAGATG
CTTCAGTCAA CTTCTCAGAG TTTTCTAACA AGTGCTCAGA GAGGTGGAAG
ACCATGTCTG CTAAAGAGAA AGGAAAATTT GAGGATATGG CAAAGGCGGA
CAAGACCCAT TATGAAAGAC AAATGAAAAC CTATATCCCT CCCAAAGGGG
AGACAAAAAA GAAGTTCAAG GATCCCAATG CACCCAAGAG GCCTCCTTCG
GCCTTCTTCC TGTTCTGCTC TGAGTATCAC CCAAAAATCA AGGAGAACA
TCCTGGCCTG TCCATTGGTG ATGTTGCGAA GAAACTGGGA GAGATGTGGA
ATAACACTGC TGCAGATGAC AAGCAGCCTG GTGAAAAGAA GGCTGCGAAG
CTGAAGGAAA AATACGAAAA GGATATTGCT GCATATCAAG CTAAAGGAAA
GCCTGAGGCA GCAAAAAAGG GAGTTGTCAA AGCTGAAAAA AGCAAGAAAA
AGAAGGAAGA GGAGGAAGAT GAGGAAGATG AAGAGGATGA GGAGGAGGAA
GATGAAGAAG ATGAAGAAGA TGATGATGAT GAA FIG. 7D
AF076674 Protein
MGKGDPKKPR GKMSSYAFFV QTCREEHKKK HSDASVNFSE FSNKCSERWK
TMSAKEKGKF EDMAKADKTH YERQMKTYIP PKGETKKKFK DPNAPKRPPS
AFFLFCSEYH PKIKGEHPGL SIGDVAKKLG EMWNNTAADD KQPGEKKAAK
LKEKYEKDIA AYQAKGKPEA AKKGVVKAEK SKKKKEEEED EEDEEDEEEE
DEEDEEDDDD E FIG. 7E
AF076676 DNA (bases 1-564)
ATGGGCAAAG GAGACCCTAA GAAGCCGAGA GGCAAAATGT CATCATATGC
ATTTTTTGTG CAAACTTGTC GGGAGGAGTG TAAGAAGAAG CACCCAGATG
CTTCAGTCAA CTTCTCAGAG TTTTCTAAGA AGTGCTCAGA GAGGTGGAAG
GCCATGTCTG CTAAAGATAA AGGAAAATTT GAAGATATGG CAAAGGTGGA
CAAAGACCGT TATGAAAGAG AAATGAAAAC CTATATCCCT CCTAAGGGG
AGACAAAAAA GAAGTTCGAG GATCCAATG CACCCAAGAG GCCTCCTTCG
GCCTTTTTGC TGTTCTGCTC TGAGTATTGC CCAAAAATCA AGGAGAGCA
TCCTGGCCTG CCTATTAGCG ATGTTGCAAA GAAACTGGTA GAGATGTGGA
ATAACACTTT TGCAGATGAC AAGCAGCTTT GTGAAAAGAA GGCTGCAAAG
CTGAAGGAAA AATACAAAAA GGATACAGCT ACATATCGAG CTAAAGGAAA
GCCTGATGCA GCAAAAAAGG GAGTTGTCAA GGCTGAAAAA AGCAAGAAAA
AGAAGGAAGA GGAG FIG. 7F
AF076676 Protein
MGKGDPKKPR GKMSSYAFFV QTCREECKKK HPDASVNFSE FSKKCSERWK
AMSAKDKGKF EDMAKVDKDR YEREMKTYIP PKGETKKKFE DSNAPKRPPS
AFLLFCSEYC PKIKGEHPGL PISDVAKKLV EMWNNTFADD KQLCEKKAAK
LKEKYKKDTA TYRAKGKPDA AKKGVVKAEK SKKKKEEE FIG. 7G
AC010149 DNA (bases 75503-76117)
ATGGACAAAG CAGATCCTAA GAAGCTGAGA GGTGAAATGT TATCATATGC
ATTTTTTGTG CAAACTTGTC AGGAGGAGCA TAAGAAGAAG AACCCAGATG
CTTCAGTCAA GTTCTCAGAG TTTTTAAAGA AGTGCTCAGA GACATGGAAG
ACCATTTTTG CTAAAGAGAA AGGAAAATTT GAAGATATGG CAAAGGCGGA
CAAGGCCCAT TATGAAAGAG AAATGAAAAC CTATATCCCT CCTAAGGGG
AGAAAAAAAA GAAGTTCAAG GATCCAATG CACCCAAGAG GCCTCCTTTG
GCCTTTTTCC TGTTCTGCTC TGAGTATCGC CCAAAAATCA AGGAGAACA
TCCTGGCCTG TCCATTGATG ATGTTGTGAA GAAACTGGCA GGGATGTGGA
ATAACACCGC TGCAGCTGAC AAGCAGTTTT ATGAAAAGAA GGCTGCAAAG

```
CTGAAGGAAA AATACAAAAA GGATATTGCT GCATATCGAG CTAAAGGAAA
GCCTAATTCA GCAAAAAGA GAGTTGTCAA GGCTGAAAAA AGCAAGAAAA
AGAAGGAAGA GGAAGAAGAT GAAGAGGATG AACAAGAGGA GGAAAATGAA
GAAGATGATG ATAAA
```

FIG. 7H
AC010149 Protein

```
MDKADPKKLR GEMLSYAFFV QTCQEEHKKK NPDASVKFSE FLKKCSETWK
TIFAKEKGKF EDMAKADKAH YEREMKTYIP PKGEKKKKFK DPNAPKRPPL
AFFLFCSEYR PKIKGEHPGL SIDDVVKKLA GMWNNTAAAD KQFYEKKAAK
LKEKYKKDIA AYRAKGKPNS AKKRVVKAEK SKKKKEEEED EEDEQEEENE
EDDDK
```

FIG. 7I
AF165168 DNA (bases 729-968)
ATGGGCAAAG GAGATCCTAA GAAGCCGAGA GGCAAAATGT CATCATGTGC
ATTTTTTGTG CAAACTTGTT GGGAGGAGCA TAAGAAGCAG TACCCAGATG
CTTCAATCAA CTTCTCAGAG TTTTCTCAGA AGTGCCCAGA GACGTGGAAG
ACCACGATTG CTAAAGAGAA AGGAAAATTT GAAGATATGC CAAAGGCAGA
CAAGGCCCAT TATGAAAGAG AAATGAAAAC CTATATACCC FIG. 7J
AF165168 Protein
MGKGDPKKPR GKMSSCAFFV QTCWEEHKKQ YPDASINFSE FSQKCPETWK
TTIAKEKGKF EDMPKADKAH YEREMKTYIP FIG. 7K
XM_063129 DNA (bases 319-558)
AAACAGAGAG GCAAAATGCC ATCGTATGTA TTTTGTGTGC AAACTTGTCC
GGAGGAGCGT AAGAAGAAAC ACCCAGATGC TTCAGTCAAC TTCTCAGAGT
TTTCTAAGAA GTGCTTAGTG AGGGGGAAGA CCATGTCTGC TAAAGAGAAA
GGACAATTTG AAGCTATGGC AAGGGCAGAC AAGGCCCGTT ACGAAAGAGA
AATGAAAACA TATATCCCTC CTAAAGGGGA GACAAAAAAA FIG. 7L
XM_063129 Protein
KQRGKMPSYV FCVQTCPEER KKKHPDASVN FSEFSKKCLV RGKTMSAKEK
GQFEAMARAD KARYEREMKT YIPPKGETKK FIG. 7M
XM_066789 DNA (bases 1-258)
ATGGGCAAAA GAGACCCTAA GCAGCCAAGA GGCAAAATGT CATCATATGC
ATTTTTTGTG CAAACTGCTC AGGAGGAGCA CAAGAAGAAA CAACTAGATG
CTTCAGTCAG TTTCTAGAG TTTTCTAAGA ACTGCTCAGA GAGGTGGAAG
ACCATGTCTG TTAAAGAGAA AGGAAAATTT GAAGACATGG CAAAGGCAGA
CAAGGCCTGT TATGAAAGAG AAATGAAAAT ATATCCCTAC TTAAAGGGGA
GACAAAAA FIG. 7N
XM_066789 Protein
MGKRDPKQPR GKMSSYAFFV QTAQEEHKKK QLDASVSFSE FSKNCSERWK
TMSVKEKGKF EDMAKADKAC YEREMKIYPY LKGRQK FIG. 7O
AF165167 DNA (bases 456-666)
ATGGGCAAAG GAGACCCTAA GAAGCCAAGA GAGAAAATGC CATCATATGC
ATTTTTTGTG CAAACTTGTA GGGAGGCACA TAAGAACAAA CATCCAGATG
CTTCAGTCAA CTCCTCAGAG TTTTCTAAGA AGTGCTCAGA GAGGTGGAAG
ACCATGCCTA CTAAACAGAA AGGAAAATTC GAAGATATGG CAAAGGCAGA
CAGGGCCCAT A FIG. 7P
AF165167 Protein
MGKGDPKKPR EKMPSYAFFV QTCREAHKNK HPDASVNSSE FSKKCSERWK
TMPTKQKGKF EDMAKADRAH

```
MPHTLWMVWVLGVIISLSKEESSNQASLSCDRNGICKGSSGSLN
SIPSGLTEAVKSLDLSNNRITYISNSDLQRCVNLQALVLTSNGI
NTIEEDSFSSLGSLEHLDLSYNYLSNLSSSWFKPLSSLTFLNLL
GNPYKTLGETSLFSHLTKLQILRVGNMDTFTKIQRKDFAGLTFL
EELEIDASDLQSYEPKSLKSIQNVSHLILHMKQHILLLEIFVDV
TSSVECLELRDTDLDTFHFSELSTGETNSLIKKFTFRNVKITDE
SLFQVMKLLNQISGLLELEFDDCTLNGVGNFRASDNDRVIDPGK
VETLTIRRLHIPRFYLFYDLSTLYSLTERVKRITVENSKVFLVP
CLLSQHLKSLEYLDLSENLMVEEYLKNSACEDAWPSLQTLILRQ
NHLASLEKTGETLLTLKNLTNIDISKNSFHSMPETCQWPEKMKY
LNLSSTRIHSVTGCIPKTLEILDVSNNNLNLFSLNLPQLKELYI
SRNKLMTLPDASLLPMLLVLKISRNAITTFSKEQLDSFHTLKTL
EAGGNNFICSCEFLSFTQEQQALAKVLIDWPANYLCDSPSHVRG
QQVQDVRLSVSECHRTALVSGMCCALFLLILLTGVLCHRFHGLW
YMKMMWAWLQAKRKPRKAPSRNICYDAFVSYSERDAYWVENLMV
QELENFNPPFKLCLHKRDFIPGKWIIDNIIDSIEKSHKTVFVLS
ENFVKSEWCKYELDFSHFRLFEENNDAAILILLEPIEKKAIPQR
FCKLRKIMNTKTYLEWPMDEAQREGFWVNLRAAIKS
```

FIG. 8

SEQUENCE LISTING

```
<160> NUMBER OF SEQ ID NOS: 46

<210> SEQ ID NO 1
<211> LENGTH: 215
<212> TYPE: PRT
<213> ORGANISM: Homo Sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Glu Asp Glu Glu Asp Glu Asp Glu
```

-continued

```
                195                 200                 205
Glu Glu Asp Asp Asp Asp Glu
    210                 215

<210> SEQ ID NO 2
<211> LENGTH: 215
<212> TYPE: PRT
<213> ORGANISM: Artificial Sequence
<220> FEATURE:
<223> OTHER INFORMATION: Mouse and rat

<400> SEQUENCE: 2

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
    210                 215

<210> SEQ ID NO 3
<211> LENGTH: 209
<212> TYPE: PRT
<213> ORGANISM: Homo Sapiens

<400> SEQUENCE: 3

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80
```

```
Pro Lys Gly Asp Lys Lys Gly Lys Lys Asp Pro Asn Ala Pro Lys
                 85                  90                  95

Arg Pro Pro Ser Ala Phe Phe Leu Phe Cys Ser Glu His Arg Pro Lys
                100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
            130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
                180                 185                 190

Glu Glu Glu Glu Glu Asp Glu Asp Glu Glu Glu Glu Asp Glu Asp Glu
            195                 200                 205

Glu
```

<210> SEQ ID NO 4
<211> LENGTH: 54
<212> TYPE: PRT
<213> ORGANISM: Artificial Sequence
<220> FEATURE:
<223> OTHER INFORMATION: Mouse/ rat/ human

<400> SEQUENCE: 4

```
Pro Asp Ala Ser Val Asn Phe Ser Glu Phe Ser Lys Lys Cys Ser Glu
 1               5                  10                  15

Arg Trp Lys Thr Met Ser Ala Lys Glu Lys Gly Lys Phe Glu Asp Met
                20                  25                  30

Ala Lys Ala Asp Lys Ala Arg Tyr Glu Arg Glu Met Lys Thr Tyr Ile
                35                  40                  45

Pro Pro Lys Gly Glu Thr
    50
```

<210> SEQ ID NO 5
<211> LENGTH: 69
<212> TYPE: PRT
<213> ORGANISM: Artificial Sequence
<220> FEATURE:
<223> OTHER INFORMATION: Mouse/ rat/ human

<400> SEQUENCE: 5

```
Asn Ala Pro Lys Arg Pro Pro Ser Ala Phe Phe Leu Phe Cys Ser Glu
 1               5                  10                  15

Tyr Arg Pro Lys Ile Lys Gly Glu His Pro Gly Leu Ser Ile Gly Asp
                20                  25                  30

Val Ala Lys Lys Leu Gly Glu Met Trp Asn Asn Thr Ala Ala Asp Asp
                35                  40                  45

Lys Gln Pro Tyr Glu Lys Lys Ala Ala Lys Leu Lys Glu Lys Tyr Glu
            50                  55                  60

Lys Asp Ile Ala Ala
65
```

<210> SEQ ID NO 6
<211> LENGTH: 216
<212> TYPE: PRT
<213> ORGANISM: Homo Sapiens

```
<400> SEQUENCE: 6

Met Gly Lys Gly Asp Pro Lys Pro Thr Gly Lys Met Ser Ser Tyr
1               5                   10                  15

Ala Phe Phe Val Gln Thr Cys Arg Glu Glu His Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Leu Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
                180                 185                 190

Asp Glu Glu Asp Glu Glu Glu Glu Asp Glu Asp Glu Glu Asp
            195                 200                 205

Glu Glu Glu Asp Asp Asp Asp Glu
    210                 215

<210> SEQ ID NO 7
<211> LENGTH: 77
<212> TYPE: PRT
<213> ORGANISM: Homo Sapiens

<400> SEQUENCE: 7

Pro Thr Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 8
<211> LENGTH: 74
<212> TYPE: PRT
<213> ORGANISM: Homo Sapiens

<400> SEQUENCE: 8

Phe Lys Asp Pro Asn Ala Pro Lys Arg Leu Pro Ser Ala Phe Phe Leu
1               5                   10                  15
```

```
Phe Cys Ser Glu Tyr Arg Pro Lys Ile Lys Gly Glu His Pro Gly Leu
            20                  25                  30

Ser Ile Gly Asp Val Ala Lys Lys Leu Gly Glu Met Trp Asn Asn Thr
        35                  40                  45

Ala Ala Asp Asp Lys Gln Pro Tyr Glu Lys Lys Ala Ala Lys Leu Lys
    50                  55                  60

Glu Lys Tyr Glu Lys Asp Ile Ala Ala Tyr
65                  70
```

<210> SEQ ID NO 9
<211> LENGTH: 648
<212> TYPE: DNA
<213> ORGANISM: Homo Sapiens

<400> SEQUENCE: 9

```
atgggcaaag gagatcctaa gaagccgaca ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaggcgga caaggcccgt tatgaaagag aaatgaaaac ctatatccct      240
cccaaagggg agacaaaaaa gaagttcaag atcccaatg cacccaagag gcttccttcg      300
gccttcttcc tcttctgctc tgagtatcgc caaaaatca aggagaaca tcctggcctg      360
tccattggtg atgttgcgaa gaaactggga gagatgtgga ataacactgc tgcagatgac     420
aagcagcctt atgaaaagaa ggctgcgaag ctgaaggaaa aatacgaaaa ggatatagct     480
gcatatcgag ctaaaggaaa gcctgatgca gcaaaaaagg gagttgtcaa ggctgaaaaa     540
agcaagaaaa agaaggaaga ggaggaagat gaggaagatg aagaggatga ggaggaggag     600
gaagatgaag aagatgaaga gatgaagaa gaagatgatg atgatgaa                   648
```

<210> SEQ ID NO 10
<211> LENGTH: 216
<212> TYPE: PRT
<213> ORGANISM: Homo Sapiens

<400> SEQUENCE: 10

```
Met Gly Lys Gly Asp Pro Lys Lys Pro Thr Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Leu Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160
```

```
Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
        180                 185                 190

Asp Glu Glu Asp Glu Glu Glu Glu Asp Glu Glu Asp Glu Glu Asp
        195                 200                 205

Glu Glu Glu Asp Asp Asp Glu
    210                 215

<210> SEQ ID NO 11
<211> LENGTH: 633
<212> TYPE: DNA
<213> ORGANISM: Homo Sapiens

<400> SEQUENCE: 11
atgggcaaag gagatcctaa gaagccgaga ggcaaaatgt catcatatgc attttttgtg    60
caaacttgtc gggaggagca taagaagaag cactcagatg cttcagtcaa cttctcagag   120
ttttctaaca gtgctcaga gaggtggaag accatgtctg ctaaagagaa aggaaaattt    180
gaggatatgg caaaggcgga caagacccat tatgaaagac aaatgaaaac ctatatccct   240
cccaaagggg agacaaaaaa gaagttcaag gatcccaatg cacccaagag gcctccttcg   300
gccttcttcc tgttctgctc tgagtatcac ccaaaaatca aggagaaca tcctggcctg    360
tccattggtg atgttgcgaa gaaactggga gagatgtgga ataacactgc tgcagatgac   420
aagcagcctg gtgaaaagaa ggctgcgaag ctgaaggaaa atacgaaaaa ggatattgct   480
gcatatcaag ctaaggaaa gcctgaggca gcaaaaaagg gagttgtcaa agctgaaaaa   540
agcaagaaaa agaaggaaga ggaggaagat gaggaagatg aagaggatga ggaggaggaa   600
gatgaagaag atgaagaaga tgatgatgat gaa                               633

<210> SEQ ID NO 12
<211> LENGTH: 211
<212> TYPE: PRT
<213> ORGANISM: Homo Sapiens

<400> SEQUENCE: 12

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Ser
                20                  25                  30

Asp Ala Ser Val Asn Phe Ser Glu Phe Ser Asn Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Thr His Tyr Glu Arg Gln Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr His Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Gly
    130                 135                 140

Glu Lys Lys Ala Ala Lys Leu Lys Glu Lys Tyr Glu Lys Asp Ile Ala
```

```
                145                 150                 155                 160
Ala Tyr Gln Ala Lys Gly Lys Pro Glu Ala Ala Lys Lys Gly Val Val
                    165                 170                 175

Lys Ala Glu Lys Ser Lys Lys Lys Glu Glu Glu Asp Glu Glu
                180                 185                 190

Asp Glu Glu Asp Glu Glu Glu Asp Glu Glu Asp Glu Glu Asp Asp
            195                 200                 205

Asp Asp Glu
    210

<210> SEQ ID NO 13
<211> LENGTH: 564
<212> TYPE: DNA
<213> ORGANISM: Homo Sapiens

<400> SEQUENCE: 13
atgggcaaag agacccctaa gaagccgaga ggcaaaatgt catcatatgc atttttgtg      60 caaacttgtc gggaggagtg taagaagaag cacccagatg cttcagtcaa cttctcagag    120
ttttctaaga agtgctcaga gaggtggaag gccatgtctg ctaaagataa aggaaaattt    180
gaagatatgg caaaggtgga caaagaccgt tatgaaagag aaatgaaaac ctatatccct    240
cctaaagggg agacaaaaaa agaagttcga gattccaatg cacccaagag gcctccttcg    300 gccttttttgc tgttctgctc tgagtattgc ccaaaaatca aggagagca tcctggcctg    360 cctattagcg atgttgcaaa gaaactggta gagatgtgga ataacacttt tgcagatgac    420
aagcagcttt gtgaaaagaa ggctgcaaag ctgaaggaaa atacaaaaa ggatacagct    480 acatatcgag ctaaaggaaa gcctgatgca gcaaaaaagg gagttgtcaa ggctgaaaaa    540
agcaagaaaa agaaggaaga ggag                                          564

<210> SEQ ID NO 14
<211> LENGTH: 188
<212> TYPE: PRT
<213> ORGANISM: Homo Sapiens

<400> SEQUENCE: 14

Met Gly Lys Gly Asp Pro Lys Lys Pro Arg Gly Lys Met Ser Ser Tyr
1               5                   10                  15

Ala Phe Phe Val Gln Thr Cys Arg Glu Glu Cys Lys Lys Lys His Pro
                20                  25                  30

Asp Ala Ser Val Asn Phe Ser Glu Phe Ser Lys Lys Cys Ser Glu Arg
            35                  40                  45

Trp Lys Ala Met Ser Ala Lys Asp Lys Gly Lys Phe Glu Asp Met Ala
    50                  55                  60

Lys Val Asp Lys Asp Arg Tyr Glu Arg Glu Met Lys Thr Tyr Ile Pro
65                  70                  75                  80

Pro Lys Gly Glu Thr Lys Lys Phe Glu Asp Ser Asn Ala Pro Lys
                85                  90                  95

Arg Pro Pro Ser Ala Phe Leu Leu Phe Cys Ser Glu Tyr Cys Pro Lys
                100                 105                 110

Ile Lys Gly Glu His Pro Gly Leu Pro Ile Ser Asp Val Ala Lys Lys
            115                 120                 125

Leu Val Glu Met Trp Asn Asn Thr Phe Ala Asp Asp Lys Gln Leu Cys
    130                 135                 140

Glu Lys Lys Ala Ala Lys Leu Lys Glu Lys Tyr Lys Lys Asp Thr Ala
145                 150                 155                 160
```

Thr Tyr Arg Ala Lys Gly Lys Pro Asp Ala Ala Lys Lys Gly Val Val
                165                 170                 175

Lys Ala Glu Lys Ser Lys Lys Lys Glu Glu Glu
        180                 185

<210> SEQ ID NO 15
<211> LENGTH: 615
<212> TYPE: DNA
<213> ORGANISM: Homo Sapiens

<400> SEQUENCE: 15
atggacaaag cagatcctaa gaagctgaga ggtgaaatgt tatcatatgc attttttgtg      60
caaacttgtc aggaggagca taagaagaag aacccagatg cttcagtcaa gttctcagag     120 ttttttaaaga agtgctcaga gacatggaag accatttttg ctaaagagaa aggaaaattt    180
gaagatatgg caaggcggga caaggcccat tatgaaagag aaatgaaaac ctatatccct     240 cctaagggg agaaaaaaaa gaagttcaag gatcccaatg cacccaagag gcctcctttg      300 gccttttttcc tgttctgctc tgagtatcgc caaaaaatca aggagaacaa tcctggcctg    360
tccattgatg atgttgtgaa gaaactggca gggatgtgga ataacaccgc tgcagctgac     420
aagcagtttt atgaaaagaa ggctgcaaag ctgaaggaaa atacaaaaaa ggatattgct     480
gcatatcgag ctaaaggaaa gcctaattca gcaaaaaaga gagttgtcaa ggctgaaaaa     540
agcaagaaaa agaaggaaga ggaagaagat gaagaggatg aacaagagga ggaaaatgaa     600
gaagatgatg ataaa                                                      615

<210> SEQ ID NO 16
<211> LENGTH: 205
<212> TYPE: PRT
<213> ORGANISM: Homo Sapiens

<400> SEQUENCE: 16

Met Asp Lys Ala Asp Pro Lys Lys Leu Arg Gly Glu Met Leu Ser Tyr
  1               5                  10                  15

Ala Phe Phe Val Gln Thr Cys Gln Glu Glu His Lys Lys Lys Asn Pro
                 20                  25                  30

Asp Ala Ser Val Lys Phe Ser Glu Phe Leu Lys Lys Cys Ser Glu Thr
             35                  40                  45

Trp Lys Thr Ile Phe Ala Lys Glu Lys Gly Lys Phe Glu Asp Met Ala
         50                  55                  60

Lys Ala Asp Lys Ala His Tyr Glu Arg Glu Met Lys Thr Tyr Ile Pro
 65                  70                  75                  80

Pro Lys Gly Glu Lys Lys Lys Phe Lys Asp Pro Asn Ala Pro Lys
                 85                  90                  95

Arg Pro Pro Leu Ala Phe Phe Leu Phe Cys Ser Glu Tyr Arg Pro Lys
                100                 105                 110

Ile Lys Gly Glu His Pro Gly Leu Ser Ile Asp Asp Val Val Lys Lys
            115                 120                 125

Leu Ala Gly Met Trp Asn Asn Thr Ala Ala Ala Asp Lys Gln Phe Tyr
        130                 135                 140

Glu Lys Lys Ala Ala Lys Leu Lys Glu Lys Tyr Lys Lys Asp Ile Ala
145                 150                 155                 160

Ala Tyr Arg Ala Lys Gly Lys Pro Asn Ser Ala Lys Lys Arg Val Val
                165                 170                 175

Lys Ala Glu Lys Ser Lys Lys Lys Lys Glu Glu Glu Glu Asp Glu Glu

```
                    180              185              190
Asp Glu Gln Glu Glu Asn Glu Glu Asp Asp Asp Lys
        195              200              205

<210> SEQ ID NO 17
<211> LENGTH: 240
<212> TYPE: DNA
<213> ORGANISM: Homo Sapiens

<400> SEQUENCE: 17
atgggcaaag gagatcctaa gaagccgaga ggcaaaatgt catcatgtgc attttttgtg      60
caaacttgtt gggaggagca taagaagcag tacccagatg cttcaatcaa cttctcagag     120
ttttctcaga gtgcccaga  gacgtggaag accacgattg ctaaagagaa aggaaaattt     180
gaagatatgc caaaggcaga caaggcccat tatgaaagag aaatgaaaac ctatataccc     240

<210> SEQ ID NO 18
<211> LENGTH: 80
<212> TYPE: PRT
<213> ORGANISM: Homo Sapiens

<400> SEQUENCE: 18

Met Gly Lys Gly Asp Pro Lys Lys Pro Arg Gly Lys Met Ser Ser Cys
1               5                   10                  15

Ala Phe Phe Val Gln Thr Cys Trp Glu Glu His Lys Lys Gln Tyr Pro
            20                  25                  30

Asp Ala Ser Ile Asn Phe Ser Glu Phe Ser Gln Lys Cys Pro Glu Thr
        35                  40                  45

Trp Lys Thr Thr Ile Ala Lys Glu Lys Gly Lys Phe Glu Asp Met Pro
    50                  55                  60

Lys Ala Asp Lys Ala His Tyr Glu Arg Glu Met Lys Thr Tyr Ile Pro
65                  70                  75                  80

<210> SEQ ID NO 19
<211> LENGTH: 240
<212> TYPE: DNA
<213> ORGANISM: Homo Sapiens

<400> SEQUENCE: 19
aaacagagag gcaaaatgcc atcgtatgta ttttgtgtgc aaacttgtcc ggaggagcgt      60
aagaagaaac acccagatgc ttcagtcaac ttctcagagt tttctaagaa gtgcttagtg     120
agggggaaga ccatgtctgc taaagagaaa ggacaatttg aagctatggc aagggcagac     180
aaggcccgtt acgaaagaga aatgaaaaca tatatccctc taaagggaga caaaaaaaa    240

<210> SEQ ID NO 20
<211> LENGTH: 80
<212> TYPE: PRT
<213> ORGANISM: Homo Sapiens

<400> SEQUENCE: 20

Lys Gln Arg Gly Lys Met Pro Ser Tyr Val Phe Cys Val Gln Thr Cys
1               5                   10                  15

Pro Glu Glu Arg Lys Lys Lys His Pro Asp Ala Ser Val Asn Phe Ser
            20                  25                  30

Glu Phe Ser Lys Lys Cys Leu Val Arg Gly Lys Thr Met Ser Ala Lys
        35                  40                  45

Glu Lys Gly Gln Phe Glu Ala Met Ala Arg Ala Asp Lys Ala Arg Tyr
    50                  55                  60
```

Glu Arg Glu Met Lys Thr Tyr Ile Pro Pro Lys Gly Glu Thr Lys Lys
65                  70                  75                  80

<210> SEQ ID NO 21
<211> LENGTH: 258
<212> TYPE: DNA
<213> ORGANISM: Homo Sapiens

<400> SEQUENCE: 21
atgggcaaaa gagaccctaa gcagccaaga ggcaaaatgt catcatatgc atttttttgtg      60 caaactgctc aggaggagca caagaagaaa caactagatg cttcagtcag tttctcagag     120
ttttctaaga actgctcaga gaggtggaag accatgtctg ttaaagagaa aggaaaattt     180
gaagacatgg caaggcaga caaggcctgt tatgaaagag aaatgaaaat atatccctac      240
ttaaagggga gacaaaaa                                                   258

<210> SEQ ID NO 22
<211> LENGTH: 86
<212> TYPE: PRT
<213> ORGANISM: Homo Sapiens

<400> SEQUENCE: 22

Met Gly Lys Arg Asp Pro Lys Gln Pro Arg Gly Lys Met Ser Ser Tyr
1               5                   10                  15

Ala Phe Phe Val Gln Thr Ala Gln Glu Glu His Lys Lys Lys Gln Leu
                20                  25                  30

Asp Ala Ser Val Ser Phe Ser Glu Phe Ser Lys Asn Cys Ser Glu Arg
            35                  40                  45

Trp Lys Thr Met Ser Val Lys Glu Lys Gly Lys Phe Glu Asp Met Ala
        50                  55                  60

Lys Ala Asp Lys Ala Cys Tyr Glu Arg Glu Met Lys Ile Tyr Pro Tyr
65                  70                  75                  80

Leu Lys Gly Arg Gln Lys
                85

<210> SEQ ID NO 23
<211> LENGTH: 211
<212> TYPE: DNA
<213> ORGANISM: Homo Sapiens

<400> SEQUENCE: 23
atgggcaaag gagaccctaa gaagccaaga gagaaaatgc catcatatgc atttttttgtg      60 caaacttgta gggaggcaca taagaacaaa catccagatg cttcagtcaa ctcctcagag     120
ttttctaaga agtgctcaga gaggtggaag accatgccta ctaaacagaa aggaaaattc     180
gaagatatgg caaaggcaga cagggcccat a                                    211

<210> SEQ ID NO 24
<211> LENGTH: 70
<212> TYPE: PRT
<213> ORGANISM: Homo Sapiens

<400> SEQUENCE: 24

Met Gly Lys Gly Asp Pro Lys Lys Pro Arg Glu Lys Met Pro Ser Tyr
1               5                   10                  15

Ala Phe Phe Val Gln Thr Cys Arg Glu Ala His Lys Asn Lys His Pro
                20                  25                  30

Asp Ala Ser Val Asn Ser Ser Glu Phe Ser Lys Lys Cys Ser Glu Arg

```
                35                  40                  45
Trp Lys Thr Met Pro Thr Lys Gln Lys Gly Lys Phe Glu Asp Met Ala
    50                  55                  60
Lys Ala Asp Arg Ala His
65                  70

<210> SEQ ID NO 25
<211> LENGTH: 54
<212> TYPE: PRT
<213> ORGANISM: Homo Sapiens

<400> SEQUENCE: 25

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
                20                  25                  30

Ala Lys Ala Asp Lys Ala Arg Tyr Glu Arg Glu Met Lys Thr Tyr Ile
                35                  40                  45

Pro Pro Lys Gly Glu Thr
    50

<210> SEQ ID NO 26
<211> LENGTH: 53
<212> TYPE: PRT
<213> ORGANISM: Homo Sapiens

<400> SEQUENCE: 26

Asp Ser Ser Val Asn Phe Ala Glu Phe Ser Lys Lys Cys Ser Glu Arg
1               5                   10                  15

Trp Lys Thr Met Ser Ala Lys Glu Lys Ser Lys Phe Glu Asp Met Ala
                20                  25                  30

Lys Ser Asp Lys Ala Arg Tyr Asp Arg Glu Met Lys Asn Tyr Val Pro
                35                  40                  45

Pro Lys Gly Asp Lys
    50

<210> SEQ ID NO 27
<211> LENGTH: 54
<212> TYPE: PRT
<213> ORGANISM: Homo Sapiens

<400> SEQUENCE: 27

Pro Glu Val Pro Val Asn Phe Ala Glu Phe Ser Lys Lys Cys Ser Glu
1               5                   10                  15

Arg Trp Lys Thr Val Ser Gly Lys Glu Lys Ser Lys Phe Asp Glu Met
                20                  25                  30

Ala Lys Ala Asp Lys Val Arg Tyr Asp Arg Glu Met Lys Asp Tyr Gly
                35                  40                  45

Pro Ala Lys Gly Gly Lys
    50

<210> SEQ ID NO 28
<211> LENGTH: 54
<212> TYPE: PRT
<213> ORGANISM: Homo Sapiens

<400> SEQUENCE: 28

Pro Asp Ala Ser Val Asn Phe Ser Glu Phe Ser Lys Lys Cys Ser Glu
1               5                   10                  15
```

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
            35                  40                  45

Pro Pro Lys Gly Glu Thr
            50

<210> SEQ ID NO 29
<211> LENGTH: 54
<212> TYPE: PRT
<213> ORGANISM: Homo Sapiens

<400> SEQUENCE: 29

Ser Asp Ala Ser Val Asn Phe Ser Glu Phe Ser Asn Lys Cys Ser Glu
 1               5                  10                  15

Arg Trp Lys Thr Met Ser Ala Lys Glu Lys Gly Lys Phe Glu Asp Met
            20                  25                  30

Ala Lys Ala Asp Lys Thr His Tyr Glu Arg Gln Met Lys Thr Tyr Ile
            35                  40                  45

Pro Pro Lys Gly Glu Thr
            50

<210> SEQ ID NO 30
<211> LENGTH: 54
<212> TYPE: PRT
<213> ORGANISM: Homo Sapiens

<400> SEQUENCE: 30

Pro Asp Ala Ser Val Asn Phe Ser Glu Phe Ser Lys Lys Cys Ser Glu
 1               5                  10                  15

Arg Trp Lys Ala Met Ser Ala Lys Asp Lys Gly Lys Phe Glu Asp Met
            20                  25                  30

Ala Lys Val Asp Lys Ala Asp Tyr Glu Arg Glu Met Lys Thr Tyr Ile
            35                  40                  45

Pro Pro Lys Gly Glu Thr
            50

<210> SEQ ID NO 31
<211> LENGTH: 54
<212> TYPE: PRT
<213> ORGANISM: Homo Sapiens

<400> SEQUENCE: 31

Pro Asp Ala Ser Val Lys Phe Ser Glu Phe Leu Lys Lys Cys Ser Glu
 1               5                  10                  15

Thr Trp Lys Thr Ile Phe Ala Lys Glu Lys Gly Lys Phe Glu Asp Met
            20                  25                  30

Ala Lys Ala Asp Lys Ala His Tyr Glu Arg Glu Met Lys Thr Tyr Ile
            35                  40                  45

Pro Pro Lys Gly Glu Lys
            50

<210> SEQ ID NO 32
<211> LENGTH: 54
<212> TYPE: PRT
<213> ORGANISM: Homo Sapiens

<400> SEQUENCE: 32

Pro Asp Ala Ser Ile Asn Phe Ser Glu Phe Ser Gln Lys Cys Pro Glu
 1               5                  10                  15

```
Thr Trp Lys Thr Thr Ile Ala Lys Glu Lys Gly Lys Phe Glu Asp Met
            20                  25                  30

Ala Lys Ala Asp Lys Ala His Tyr Glu Arg Glu Met Lys Thr Tyr Ile
        35                  40                  45

Pro Pro Lys Gly Glu Thr
        50

<210> SEQ ID NO 33
<211> LENGTH: 38
<212> TYPE: PRT
<213> ORGANISM: Homo Sapiens

<400> SEQUENCE: 33

Pro Asp Ala Ser Val Asn Ser Ser Glu Phe Ser Lys Lys Cys Ser Glu
  1               5                  10                  15

Arg Trp Lys Thr Met Pro Thr Lys Gln Gly Lys Phe Glu Asp Met Ala
            20                  25                  30

Lys Ala Asp Arg Ala His
        35

<210> SEQ ID NO 34
<211> LENGTH: 54
<212> TYPE: PRT
<213> ORGANISM: Homo Sapiens

<400> SEQUENCE: 34

Pro Asp Ala Ser Val Asn Phe Ser Glu Phe Ser Lys Lys Cys Leu Val
  1               5                  10                  15

Arg Gly Lys Thr Met Ser Ala Lys Glu Lys Gly Gln Phe Glu Ala Met
            20                  25                  30

Ala Arg Ala Asp Lys Ala Arg Tyr Glu Arg Glu Met Lys Thr Tyr Ile
        35                  40                  45

Pro Pro Lys Gly Glu Thr
        50

<210> SEQ ID NO 35
<211> LENGTH: 54
<212> TYPE: PRT
<213> ORGANISM: Homo Sapiens

<400> SEQUENCE: 35

Leu Asp Ala Ser Val Ser Phe Ser Glu Phe Ser Asn Lys Cys Ser Glu
  1               5                  10                  15

Arg Trp Lys Thr Met Ser Val Lys Glu Lys Gly Lys Phe Glu Asp Met
            20                  25                  30

Ala Lys Ala Asp Lys Ala Cys Tyr Glu Arg Glu Met Lys Ile Tyr Pro
        35                  40                  45

Tyr Leu Lys Gly Arg Gln
        50

<210> SEQ ID NO 36
<211> LENGTH: 84
<212> TYPE: PRT
<213> ORGANISM: Homo Sapiens

<400> SEQUENCE: 36

Gly Lys Gly Asp Pro Lys Lys Pro Arg Gly Lys Met Ser Ser Tyr Ala
  1               5                  10                  15

Phe Phe Val Gln Thr Cys Arg Glu Glu His Lys Lys Lys His Pro Asp
```

```
                    20                  25                  30
Ala Ser Val Asn Phe Ser Glu Phe Ser Lys Lys Cys Ser Glu Arg Trp
            35                  40                  45
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 37
<211> LENGTH: 74
<212> TYPE: PRT
<213> ORGANISM: Homo Sapiens

<400> SEQUENCE: 37

Phe Lys Asp Pro Asn Ala Pro Lys Arg Pro Pro Ser Ala Phe Phe Leu
1               5                   10                  15
Phe Cys Ser Glu Tyr Arg Pro Lys Ile Lys Gly Glu His Pro Gly Leu
                20                  25                  30
Ser Ile Gly Asp Val Ala Lys Lys Leu Gly Glu Met Trp Asn Asn Thr
            35                  40                  45
Ala Ala Asp Asp Lys Gln Pro Tyr Glu Lys Lys Ala Ala Lys Leu Lys
        50                  55                  60
Glu Lys Tyr Glu Lys Asp Ile Ala Ala Tyr
65                  70

<210> SEQ ID NO 38
<211> LENGTH: 74
<212> TYPE: PRT
<213> ORGANISM: Homo Sapiens

<400> SEQUENCE: 38

Lys Lys Asp Pro Asn Ala Pro Lys Arg Pro Pro Ser Ala Phe Phe Leu
1               5                   10                  15
Phe Cys Ser Glu His Arg Pro Lys Ile Lys Ser Glu His Pro Gly Leu
                20                  25                  30
Ser Ile Gly Asp Thr Ala Lys Lys Leu Gly Glu Met Trp Ser Glu Gln
            35                  40                  45
Ser Ala Lys Asp Lys Gln Pro Tyr Glu Gln Lys Ala Ala Lys Leu Lys
        50                  55                  60
Glu Lys Tyr Glu Lys Asp Ile Ala Ala Tyr
65                  70

<210> SEQ ID NO 39
<211> LENGTH: 74
<212> TYPE: PRT
<213> ORGANISM: Homo Sapiens

<400> SEQUENCE: 39

Phe Lys Asp Pro Asn Ala Pro Lys Arg Leu Pro Ser Ala Phe Phe Leu
1               5                   10                  15
Phe Cys Ser Glu Tyr Arg Pro Lys Ile Lys Gly Glu His Pro Gly Leu
                20                  25                  30
Ser Ile Gly Asp Val Ala Lys Lys Leu Gly Glu Met Trp Asn Asn Thr
            35                  40                  45
Ala Ala Asp Asp Lys Gln Pro Tyr Glu Lys Lys Ala Ala Lys Leu Lys
        50                  55                  60
```

```
Glu Lys Tyr Glu Lys Asp Ile Ala Ala Tyr
65                  70
```

<210> SEQ ID NO 40
<211> LENGTH: 74
<212> TYPE: PRT
<213> ORGANISM: Homo Sapiens

<400> SEQUENCE: 40

```
Phe Lys Asp Pro Asn Ala Pro Lys Arg Pro Pro Ser Ala Phe Phe Leu
1               5                   10                  15

Phe Cys Ser Glu Tyr His Pro Lys Ile Lys Gly Glu His Pro Gly Leu
                20                  25                  30

Ser Ile Gly Asp Val Ala Lys Lys Leu Gly Glu Met Trp Asn Asn Thr
            35                  40                  45

Ala Ala Asp Asp Lys Gln Pro Gly Glu Lys Ala Ala Lys Leu Lys
        50                  55                  60

Glu Lys Tyr Glu Lys Asp Ile Ala Ala Tyr
65                  70
```

<210> SEQ ID NO 41
<211> LENGTH: 74
<212> TYPE: PRT
<213> ORGANISM: Homo Sapiens

<400> SEQUENCE: 41

```
Phe Lys Asp Ser Asn Ala Pro Lys Arg Pro Pro Ser Ala Phe Leu Leu
1               5                   10                  15

Phe Cys Ser Glu Tyr Cys Pro Lys Ile Lys Gly Glu His Pro Gly Leu
                20                  25                  30

Pro Ile Ser Asp Val Ala Lys Lys Leu Val Glu Met Trp Asn Asn Thr
            35                  40                  45

Phe Ala Asp Asp Lys Gln Leu Cys Glu Lys Lys Ala Ala Lys Leu Lys
        50                  55                  60

Glu Lys Tyr Lys Lys Asp Thr Ala Thr Tyr
65                  70
```

<210> SEQ ID NO 42
<211> LENGTH: 74
<212> TYPE: PRT
<213> ORGANISM: Homo Sapiens

<400> SEQUENCE: 42

```
Phe Lys Asp Pro Asn Ala Pro Lys Arg Pro Pro Ser Ala Phe Phe Leu
1               5                   10                  15

Phe Cys Ser Glu Tyr Arg Pro Lys Ile Lys Gly Glu His Pro Gly Leu
                20                  25                  30

Ser Ile Gly Asp Val Val Lys Lys Leu Ala Gly Met Trp Asn Asn Thr
            35                  40                  45

Ala Ala Ala Asp Lys Gln Phe Tyr Glu Lys Lys Ala Ala Lys Leu Lys
        50                  55                  60

Glu Lys Tyr Lys Lys Asp Ile Ala Ala Tyr
65                  70
```

<210> SEQ ID NO 43
<211> LENGTH: 92
<212> TYPE: PRT
<213> ORGANISM: Homo Sapiens

<400> SEQUENCE: 43

```
Phe Lys Asp Pro Asn Ala Pro Lys Arg Pro Ser Ala Phe Phe Leu
 1               5                  10                  15

Phe Cys Ser Glu Tyr Arg Pro Lys Ile Lys Gly Glu His Pro Gly Leu
             20                  25                  30

Ser Ile Gly Asp Val Ala Lys Lys Leu Gly Glu Met Trp Asn Asn Thr
             35                  40                  45

Ala Ala Asp Asp Lys Gln Pro Tyr Glu Lys Lys Ala Ala Lys Leu Lys
     50                  55                  60

Glu Lys Tyr Glu Lys Asp Ile Ala Ala Tyr Arg Ala Lys Gly Lys Pro
 65                  70                  75                  80

Asp Ala Ala Lys Lys Gly Val Val Lys Ala Glu Lys
                 85                  90

<210> SEQ ID NO 44
<211> LENGTH: 20
<212> TYPE: PRT
<213> ORGANISM: Homo Sapiens

<400> SEQUENCE: 44

Asn Ala Pro Lys Arg Pro Ser Ala Phe Phe Leu Phe Cys Ser Glu
 1               5                  10                  15

Tyr Arg Pro Lys
             20

<210> SEQ ID NO 45
<211> LENGTH: 20
<212> TYPE: PRT
<213> ORGANISM: Homo Sapiens

<400> SEQUENCE: 45

Phe Lys Asp Pro Asn Ala Pro Lys Arg Leu Pro Ser Ala Phe Phe Leu
 1               5                  10                  15

Phe Cys Ser Glu
             20

<210> SEQ ID NO 46
<211> LENGTH: 784
<212> TYPE: PRT
<213> ORGANISM: Homo Sapiens

<400> SEQUENCE: 46

Met Pro His Thr Leu Trp Met Val Trp Val Leu Gly Val Ile Ile Ser
 1               5                  10                  15

Leu Ser Lys Glu Glu Ser Ser Asn Gln Ala Ser Leu Ser Cys Asp Arg
             20                  25                  30

Asn Gly Ile Cys Lys Gly Ser Ser Gly Ser Leu Asn Ser Ile Pro Ser
             35                  40                  45

Gly Leu Thr Glu Ala Val Lys Ser Leu Asp Leu Ser Asn Asn Arg Ile
     50                  55                  60

Thr Tyr Ile Ser Asn Ser Asp Leu Gln Arg Cys Val Asn Leu Gln Ala
 65                  70                  75                  80

Leu Val Leu Thr Ser Asn Gly Ile Asn Thr Ile Glu Glu Asp Ser Phe
                 85                  90                  95

Ser Ser Leu Gly Ser Leu Glu His Leu Asp Leu Ser Tyr Asn Tyr Leu
                100                 105                 110

Ser Asn Leu Ser Ser Ser Trp Phe Lys Pro Leu Ser Ser Leu Thr Phe
            115                 120                 125
```

```
Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
    370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
    450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
    530                 535                 540

Thr Gln Glu Gln Gln Ala Leu Ala Lys Val Leu Ile Asp Trp Pro Ala
```

-continued

```
545                 550                 555                 560
Asn Tyr Leu Cys Asp Ser Pro Ser His Val Arg Gly Gln Gln Val Gln
                565                 570                 575
Asp Val Arg Leu Ser Val Ser Glu Cys His Arg Thr Ala Leu Val Ser
            580                 585                 590
Gly Met Cys Cys Ala Leu Phe Leu Leu Ile Leu Leu Thr Gly Val Leu
            595                 600                 605
Cys His Arg Phe His Gly Leu Trp Tyr Met Lys Met Met Trp Ala Trp
            610                 615                 620
Leu Gln Ala Lys Arg Lys Pro Arg Lys Ala Pro Ser Arg Asn Ile Cys
625                 630                 635                 640
Tyr Asp Ala Phe Val Ser Tyr Ser Glu Arg Asp Ala Tyr Trp Val Glu
                645                 650                 655
Asn Leu Met Val Gln Glu Leu Glu Asn Phe Asn Pro Pro Phe Lys Leu
                660                 665                 670
Cys Leu His Lys Arg Asp Phe Ile Pro Gly Lys Trp Ile Ile Asp Asn
            675                 680                 685
Ile Ile Asp Ser Ile Glu Lys Ser His Lys Thr Val Phe Val Leu Ser
        690                 695                 700
Glu Asn Phe Val Lys Ser Glu Trp Cys Lys Tyr Glu Leu Asp Phe Ser
705                 710                 715                 720
His Phe Arg Leu Phe Glu Glu Asn Asn Asp Ala Ala Ile Leu Ile Leu
                725                 730                 735
Leu Glu Pro Ile Glu Lys Lys Ala Ile Pro Gln Arg Phe Cys Lys Leu
            740                 745                 750
Arg Lys Ile Met Asn Thr Lys Thr Tyr Leu Glu Trp Pro Met Asp Glu
            755                 760                 765
Ala Gln Arg Glu Gly Phe Trp Val Asn Leu Arg Ala Ala Ile Lys Ser
            770                 775                 780
```

INHIBITORS OF THE INTERACTION BETWEEN HMGB POLYPEPTIDES AND TOLL-LIKE RECEPTOR 2 AS ANTI-INFLAMMATORY AGENTS

GOVERNMENT SUPPORT

The invention was supported, in whole or in part, by a grant GM 62508KT from the National Institutes of Health. The Government has certain rights in the invention.

BACKGROUND OF THE INVENTION

Inflammation is often induced by proinflammatory cytokines, such as tumor necrosis factor (TNF), interleukin (IL)-1α, IL-1β, IL-6, platelet-activating factor (PAF), macrophage migration inhibitory factor (MIF), and other compounds. These proinflammatory cytokines are produced by several different cell types, including immune cells (for example, monocytes, macrophages and neutrophils), and non-immune cells such as fibroblasts, osteoblasts, smooth muscle cells, epithelial cells, and neurons.

These proinflammatory cytokines are part of an inflammatory cytokine cascade that contributes to the occurrence of inflammation. In addition to mediation of inflammation, early proinflammatory cytokines (e.g., TNF, IL-1, etc.) induce the late release of high mobility group box 1 (HMGB1; also known as HMG-1 and HMG1), a protein that accumulates in serum and mediates delayed lethality and further induction of early proinflammatory cytokines.

HMGB1 was first identified as the founding member of a family of DNA-binding proteins termed high mobility group box (HMGB) proteins that are critical for DNA structure and stability. It was identified nearly 40 years ago as a ubiquitously expressed nuclear protein that binds double-stranded DNA without sequence specificity. The HMGB1 protein has three domains: two DNA binding motifs termed HMGB A and HMGB B boxes, and an acidic carboxyl terminus. The two HMGB boxes are highly conserved 80 amino acid, L-shaped domains.

Recent evidence has implicated HMGB1 as a mediator of a number of inflammatory conditions (U.S. Pat. No. 6,303,321). The delayed kinetics of HMGB1 appearance during endotoxemia makes it a potentially good therapeutic target, but little is known about the molecular basis of HMGB1 signaling and toxicity.

SUMMARY OF THE INVENTION

It has been discovered that HMGB polypeptides bind Toll-like receptor 2 (TLR2) and can mediate biological effects through TLR2. It has also been discovered that inhibition of the interaction between HMGB and TLR2 can decrease or prevent inflammation. Therefore, agents that inhibit the interaction of an HMGB polypeptide with TLR2 can be used to treat inflammatory conditions.

Accordingly, in a first aspect, the invention features a method of treating an inflammatory condition in an individual, comprising administering to the individual an effective amount of an agent that inhibits the interaction between an HMGB polypeptide or a functional equivalent thereof and a TLR2, with the proviso that the agent is not an antibody that binds to an HMGB1 polypeptide. In one embodiment, the agent binds a TLR2 and inhibits binding by an HMGB polypeptide or functional equivalent thereof.

In another aspect, the invention features a method of inhibiting the release of a proinflammatory cytokine from a cell, comprising administering to the cell an effective amount of an agent that inhibits the interaction between an HMGB polypeptide or functional equivalent thereof and a TLR2, with the proviso that the agent is not an antibody that binds to an HMGB1 polypeptide. In one embodiment, the agent binds a TLR2 and inhibits binding by an HMGB polypeptide or functional equivalent thereof.

In another aspect, the invention features a method of determining whether an agent inhibits inflammation, comprising contacting a TLR2 with the agent and an HMGB polypeptide or a functional equivalent thereof; and detecting binding of an HMGB polypeptide to the TLR2, wherein an agent that decreases binding of the HMGB polypeptide or functional equivalent to the TLR2 relative to a suitable control is an agent that inhibits inflammation.

In another aspect, the invention features an ex vivo method of determining whether an agent inhibits inflammation, comprising contacting a cell comprising a TLR2 with the agent and an HMGB polypeptide or functional equivalent thereof; and measuring release of a proinflammatory cytokine from the cell, wherein an agent that decreases release of the proinflammatory cytokine from the cell relative to a suitable control is an agent that inhibits inflammation.

The present invention provides the advantage of identifying new agents and/or methods for treating (or preventing) inflammatory conditions, as well as methods for identifying such agents. These agents act at the level of the interaction between HMGB polypeptides and TLR2.

stably transfected with TLR2 (HEK-TLR2). HEK cells over-expressing TLR2 were plated in a 24-well culture plate and treated with HMGB1 (expressed in CHO cells) at the concentrations indicated for 18 hours. IL-8 release in conditioned supernatants was measured by ELISA. Data shown are mean±SEM, n=3 or more.

Figures 3A, 3B:
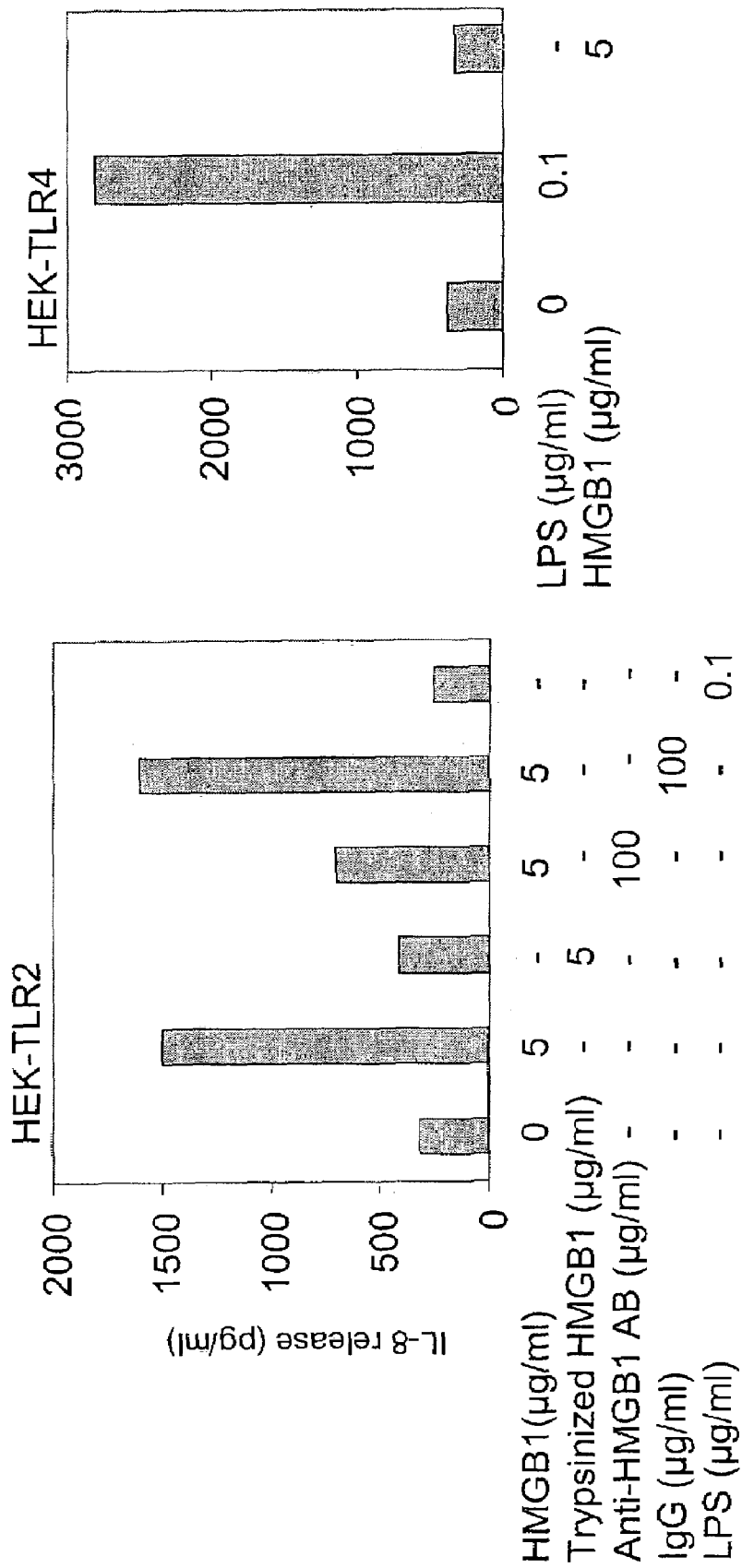

FIG. 3A is a histogram showing the specificity of HMGB1-induced IL-8 release in HEK-TLR2 cells under various treatment conditions, assessed by measuring IL-8 release from the cells. HEK-TLR2-expressing cells in a 24-well plate were stimulated with HMGB1 (trypsinized or intact, in the indicated amounts) or LPS, as indicated for 18 hours, with or without IgG-purified anti-HMGB1 antibody or non-immune IgG added, as indicated. LPS was sonicated for 20 minutes before use. N=3 separate experiments.

FIG. 3B is a histogram showing the specificity of HMGB1-induced IL-8 release in HEK-TLR4 cells under various treatment conditions, assessed by measuring IL-8 release from the cells. HEK-TLR4-expressing cells in a 24-well plate were stimulated with HMGB1 (intact, in the indicated amounts) or LPS as indicated for 18 hours (sonicated for 20 minutes before use). N=3 separate experiments.

Figures 4A, 4B:
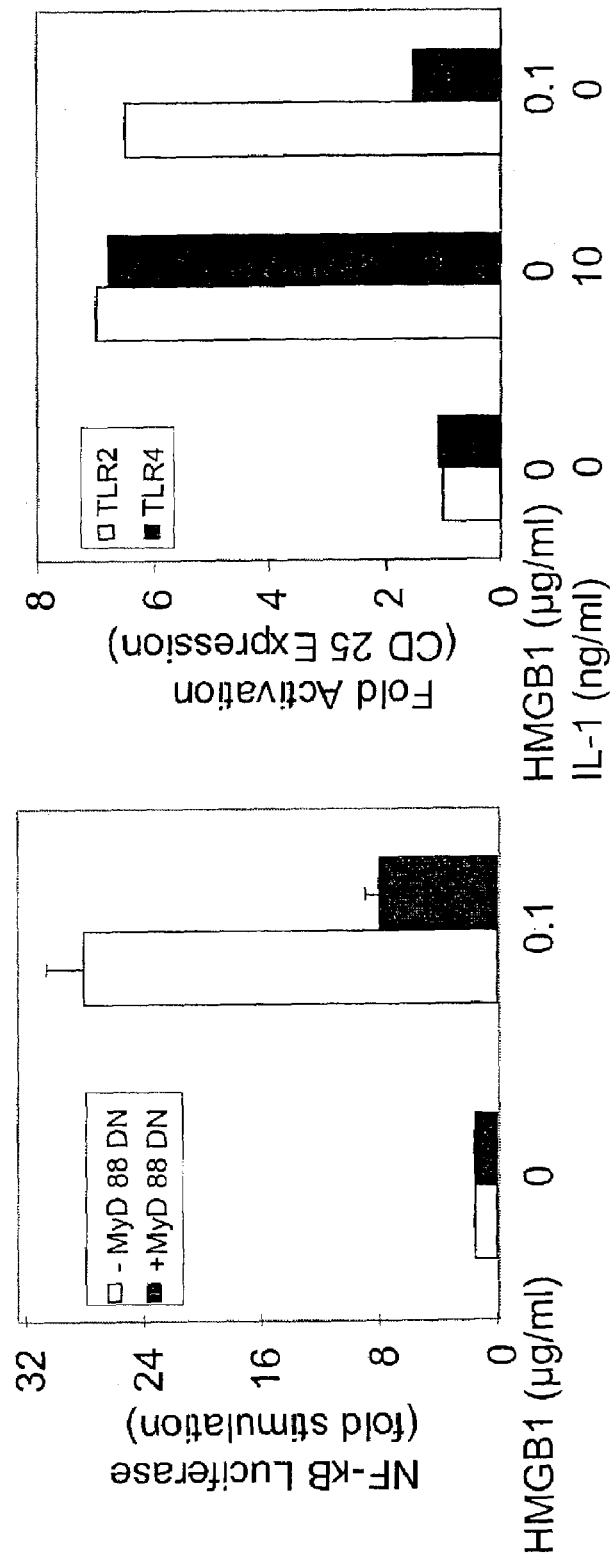

FIG. 4A is a histogram showing the effect of dominant negative MyD 88 on NF-κB-dependent luciferase activity. Sub-confluent RAW 264.7 cells (over-expressing either wild type or mutant MyD88 and an NF-κB-dependent luciferase reporter) in 24-well plates were stimulated with HMGB1 (100 ng/ml) for 5 hours. Cells were then harvested and luciferase activity was measured. All transfections were performed in triplicate, repeated at least three times, and a single representative experiment is shown. Data are expressed as the ratio (fold-activation) of average luciferase values from un-stimulated and stimulated cells (subtracted for background)±SD.

FIG. 4B is a histogram showing the effect of HMGB1 or IL-1 on NF-κB-dependent CD25 expression in CHO cells transfected with either TLR2 or TLR4. CHO/TLR2 and CHO/TLR4 cells were seeded into 24-well tissue culture plates and used at 90% confluence. Cells were stimulated with IL-1 (10 ng/ml) or purified HMGB1 (100 ng/ml) for 18 hours. Following stimulation, cells were stained with a PE-labeled anti-CD25 monoclonal antibody and surface expression of CD25 was measured by flow cytometry. Data are expressed as the ratio (fold-activation) of the percent of CD25 positive cells in un-stimulated and stimulated cell populations that were gated to exclude the lowest 5% of cells based on mean FL1 fluorescence.

FIG. 5A is a scanned confocal microscopic image of RAW 264.7 cells administered FITC-labeled HMGB1. Macrophage-like RAW 264.7 cells were plated in an 8-well slide chamber and used at 70% confluence. Cells were incubated with FITC-labeled HMGB1 at 1 μg/ml for 15 minutes at 37° C. Cells were then washed 3 times with PBS and fixed for 15 minutes at room temperature in 4% paraformaldehyde-PBS solution (pH 7.2). After fixing, cells were washed with PBS once and mounted for viewing by fluorescent confocal microscopy. Magnification: X40.

FIG. 5B is a scanned confocal microscopic image of RAW 264.7 cells administered anti-TLR2 antibody and FITC-labeled HMGB1. Macrophage-like RAW 264.7 cells were plated in an 8-well slide chamber and used at 70% confluence. Cells were pre-incubated with anti-TLR2 antibody at 1 μg/ml for 20 minutes at 37° C. in Opti-MEM I medium, and then FITC-labeled HMGB1 was added at 1 μg/ml and the cells were incubated for an additional 15 minutes at 37° C. Cells were washed 3 times with PBS and fixed for 15 minutes at room temperature in 4% paraformaldehyde-PBS solution (pH 7.2). After fixing, cells were washed with PBS once and mounted for viewing by fluorescent confocal microscopy. Magnification: X40.

FIG. 5C is a scanned confocal microscopic image of RAW 264.7 cells administered anti-TLR4 antibody and FITC-labeled HMGB1. Macrophage-like RAW 264.7 cells were plated in an 8-well slide chamber and used at 70% confluence. Cells were pre-incubated with anti-TLR4 antibody at 1 μg/ml for 20 minutes at 37° C. in Opti-MEM I medium, and then FITC-labeled HMGB1 was added at 1 μg/ml and the cells were incubated for an additional 15 minutes at 37° C. Cells were washed 3 times with PBS and fixed for 15 minutes at room temperature in 4% paraformaldehyde-PBS solution (pH 7.2). After fixing, cells were washed with PBS once and mounted for viewing by fluorescent confocal microscopy. Magnification: X40.

FIG. 6A is the amino acid sequence of a human HMGB1 polypeptide (SEQ ID NO:1).

FIG. 6B is the amino acid sequence of rat and mouse HMGB1 (SEQ ID NO:2).

FIG. 6C is the amino acid sequence of human HMGB2 (SEQ ID NO:3).

FIG. 6D is the amino acid sequence of a human, mouse, and rat HMGB1 A box polypeptide (SEQ ID NO:4).

FIG. 6E is the amino acid sequence of a human, mouse, and rat HMGB1 B box polypeptide (SEQ ID NO:5).

FIG. 7A is the nucleic acid sequence of HMG1L10 (SEQ ID NO: 9) encoding an HMGB polypeptide.

FIG. 7B is the polypeptide sequence of HMG1L10 (SEQ ID NO:10), which is an HMGB polypeptide. p FIG. 7C is the nucleic acid sequence of HMG1L1 (SEQ ID NO: 11) encoding an HMGB polypeptide.

FIG. 7D is the polypeptide sequence of HMG1L1 (SEQ ID NO:12), which is an HMGB polypeptide.

FIG. 7E is the nucleic acid sequence of HMG1L4 (SEQ ID NO: 13) encoding an HMGB polypeptide.

FIG. 7F is the polypeptide sequence of HMG1L4 (SEQ ID NO:14), which is an HMGB polypeptide.

FIG. 7G is the nucleic acid sequence of the HMG polypeptide of the BAC clone RP11-395A23 (SEQ ID NO: 15) encoding an HMGB polypeptide.

FIG. 7H is the polypeptide sequence of the HMG polypeptide of the BAC clone RP11-395A23 (SEQ ID NO: 16), which is an HMGB polypeptide.

FIG. 7I is the nucleic acid sequence of HMG1L9 (SEQ ID NO: 17) encoding an HMGB polypeptide.

FIG. 7J is the polypeptide sequence of HMG1L9 (SEQ ID NO:18), which is an HMGB polypeptide.

FIG. 7K is the nucleic acid sequence of LOC122441 (SEQ ID NO: 19) encoding an HMGB polypeptide.

FIG. 7L is the polypeptide sequence of LOC122441 (SEQ ID NO:20), which is an HMGB polypeptide.

FIG. 7M is the nucleic acid sequence of LOC139603 (SEQ ID NO: 21) encoding an HMGB polypeptide.

FIG. 7N is the polypeptide sequence of LOC139603 (SEQ ID NO:22), which is an HMGB polypeptide.

FIG. 7O is the nucleic acid sequence of HMG1L8 (SEQ ID NO: 23) encoding an HMGB polypeptide.

FIG. 7P is the polypeptide sequence of HMG1L8 (SEQ ID NO:24), which is an HMGB polypeptide.

FIG. 8 is the polypeptide sequence of human TLR2 (SEQ ID NO: 46).

DETAILED DESCRIPTION OF THE INVENTION

The present invention relates to the discovery that HMGB biological activity is mediated through binding of HMGB to Toll-like receptor 2 (TLR2). Therefore, the biological activity of HMGB can be inhibited by inhibiting binding of HMGB to TLR2. This inhibition can be achieved by providing an agent that binds TLR2 and prevents binding by an HMGB polypeptide. Alternatively, the agent can bind the HMGB polypeptide and prevent the polypeptide from binding to TLR2. As HMGB mediates release of proinflammatory cytokines from a cell, agents that inhibit the interaction between HMGB and TLR2 can be used to prevent release of one or more proinflammatory cytokines from the cell. These proinflammatory cytokines contribute to many inflammatory conditions; therefore, agents that inhibit the interaction between HMGB and TLR2 can be used to treat or inhibit inflammatory conditions mediated through the inflammatory cytokine cascade. The present invention also features methods of identifying agents that inhibit the interaction between HMGB and TLR2. Agents identified through such screening methods can be used to treat an inflammatory condition, or to inhibit release of a proinflammatory cytokine from a cell.

HMGB Polypeptides

As used herein, an "HMGB polypeptide" is polypeptide that has at least 60%, more preferably, at least 70%, 75%, 80%, 85%, or 90%, and most preferably at least 95% sequence identity to a sequence selected from SEQ ID NO:1, SEQ ID NO:2, SEQ ID NO:3, or SEQ ID NO:6 (MGKGDPKKPTGKMSSYAFFVQTCREEHKKKH PDASVNFSEFSKKCSERWKTMSAKEKGKFEDMAKADKARYEREMKTYIPPKG ETKKKFKDPNAPKRLPSAFFLFCSEYRPKIKGEHPGLSIGDVAKKLGEMWNNTA ADDKQPYEKKAAKLKEKYEKDIAAYRAKGKPDAAKKGVVKAEKSKKKKEEE EDEEDEEDEEEEEDEEDEEDEEEDDDDE) (as determined, for example, using the BLAST program and parameters described herein) and increases inflammation and/or increases release of a proinflammatory cytokine from a cell. In one embodiment, the HMGB polypeptide has one of the above biological activities. Typically, the HMGB polypeptide has both of the above biological activities. The term "polypeptide" refers to a polymer of amino acids, and not to a specific length; thus, peptides, oligopeptides and proteins are included within the definition of a polypeptide. Preferably, the HMGB polypeptide is a mammalian HMGB polypeptide, for example, a human HMGB1 polypeptide. Examples of an HMGB polypeptide include a polypeptide comprising or consisting of the sequence of SEQ ID NO:1, SEQ ID NO:2, SEQ ID NO:3, or SEQ ID NO:6.

Other examples of HMGB polypeptides are described in GenBank Accession Numbers AAA64970, AAB08987, P07155, AAA20508, S29857, P09429, NP_002119, CAA31110, S02826, U00431, X67668, NP_005333, NM_016957, and J04179, the entire teachings of which are incorporated herein by reference. Additional examples of HMGB polypeptides include, but are not limited to mammalian HMG1 ((HMGB1) as described, for example, in GenBank Accession Number U51677), HMG2 ((HMGB2) as described, for example, in GenBank Accession Number M83665), HMG-2A ((HMGB3, HMG-4) as described, for example, in GenBank Accession Numbers NM_005342 and NP_005333), HMG14 (as described, for example, in GenBank Accession Number P05114), HMG17 (as described, for example, in GenBank Accession Number X13546), HMGI (as described, for example, in GenBank Accession Number L17131), and HMGY (as described, for example, in GenBank Accession Number M23618); nonmammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (Xenopus), HMG D (as described, for example, in GenBank Accession Number X71138) and HMG Z (as described, for example, in GenBank Accession Number X71139) (Drosophila); NHP10 protein (HMG protein homolog NHP 1) (as described, for example, in GenBank Accession Number Z48008) (yeast); non-histone chromosomal protein (as described, for example, in GenBank Accession Number O00479) (yeast); HMG 1/2 like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB009451), ste 11 (as described, for example, in GenBank Accession Number x53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ001183), SOX 12 (as described, for example, in GenBank Accession Number X73039) and SOX 21 (as described, for example, in GenBank Accession Number AF107044)); lymphoid specific factor (LEF-1) (as described, for example, in GenBank Accession Number X58636); T-cell specific transcription factor (TCF-1) (as described, for example, in GenBank Accession Number X59869); MTT1 (as described, for example, in GenBank Accession Number M62810); and SP100-HMG nuclear autoantigen (as described, for example, in GenBank Accession Number U36501).

Other examples of HMGB proteins are polypeptides encoded by HMGB nucleic acid sequences having GenBank Accession Numbers NG_000897 (HMG1L10) (and in particular by nucleotides 658–1305 of NG_000897, as shown in FIGS. 7A and 7B); AF076674 (HMG1L1) (and in particular by nucleotides 1-633 of AF076674, as shown in FIGS. 7C and 7D; AF076676 (HMG1L4) (and in particular by nucleotides 1-564 of AF076676, as shown in FIGS. 7E and 7F); AC010149 (HMG sequence from BAC clone RP11-395A23) (and in particular by nucleotides 75503-76117 of AC010149, as shown in FIGS. 7G and 7H); AF165168 (HMG1L9) (and in particular by nucleotides 729–968 of AF165168, as shown in FIGS. 7I and 7J); XM_063129 (LOC122441) (and in particular by nucleotides 319–558 of XM_063129, as shown in FIGS. 7K and 7L); XM_066789 (LOC139603) (and in particular by nucleotides 1-258 of XM_066789, as shown in FIGS. 7M and 7N); and AF165167 (HMG1L8) (and in particular by nucleotides 456–666 of AF165167, as shown in FIGS. 7O and 7P).

Optionally, the HMGB polypeptide is a substantially pure, or substantially pure and isolated polypeptide that has been separated from components that naturally accompany it. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell (e.g., in a "fusion protein") and still be "isolated" or "purified." It is understood, however, that preparations in which the polypeptide is not purified to homogeneity are useful. For example, the polypeptide may be in an unpurified form, for example, in a cell, cell milieu, or cell extract. The critical feature is that the preparation allows for the desired function of the polypeptide, even in the presence of considerable amounts of other components.

Functional equivalents of HMGB (proteins or polypeptides that have one or more of the biological activities of an HMGB polypeptide) can also be used in the methods of the present invention. Biologically active fragments, sequence variants, post-translational modifications, and chimeric or fusion proteins comprising the protein, biologically active fragment, or variant are examples of functional equivalents of a protein. Variants include a substantially homologous polypeptide encoded by the same genetic locus in an organism, i.e., an allelic variant, as well as other splicing variants. Variants also encompass polypeptides derived from other genetic loci in an organism, but having substantial homology to the protein of interest, for example, an HMGB protein as described herein.

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science, 244:1081–1085 (1989)). The latter procedure introduces single alanine mutations at every residue in the molecule. The resulting mutant molecules are then tested for biological activity in vitro. Sites that are critical for polypeptide activity can also be determined by structural analysis such as crystallization, nuclear magnetic resonance or photoaffinity labeling (Smith et al., J. Mol. Biol., 224:899–904 (1992); de Vos et al., Science, 255:306–312 (1992)).

HMGB functional equivalents also encompass polypeptides having a lower degree of identity but having sufficient similarity so as to perform one or more of the same functions performed by an HMGB polypeptide. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found in Bowie et al., Science, 247:1306–1310 (1990).

HMGB functional equivalents also include polypeptide fragments of HMGB. Fragments can be derived from an HMGB polypeptide or fragments of HMGB variants. As used herein, a fragment comprises at least 6 contiguous amino acids. Useful fragments include those that retain one or more of the biological activities of the polypeptide. Examples of HMGB biologically active fragments include the B box, as well as fragments of the B box, for example, the first 20 amino acids of the B box (e.g. the first 20 amino acids of SEQ ID NOs: 5 (SEQ ID NO: 44) or 8 (SEQ ID NO: 45)).

Biologically active fragments (peptides which are, for example, 6, 9, 12, 15, 16, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, or post-translation modification sites. Example of domains include the A box and/or the B box as described herein.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention also provides uses and methods for chimeric or fusion polypeptides containing an HMGB polypeptide, biologically active fragment thereof, or variant thereof as functional equivalents of HMGB. These chimeric proteins comprise an HMGB polypeptide or functional equivalent thereof operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment the fusion polypeptide does not affect function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example, β-galactosidase fusions, yeast two-hybrid GAL fusions, poly-His fusions, FLAG-tagged fusions, GFP fusions, and Ig fusions. Such fusion polypeptides can facilitate the purification of recombinant polypeptide. In certain host cells (e.g., mammalian host cells) expression and/or secretion of a polypeptide can be increased by using a heterologous signal sequence. Therefore, in another embodiment, the fusion polypeptide contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al., Journal of Molecular Recognition 8:52–58 (1995) and Johanson et al., The Journal of Biological Chemistry, 270 (16):9459–9471 (1995). Thus, this invention also encompasses soluble fusion polypeptides containing a polypeptide of the invention and various portions of the constant regions of heavy or light chains of immunoglobulins of various subclass (IgG, IgM, IgA, IgE).

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992). Moreover, many expression vectors are commercially available that already encode a fusion moiety (e.g., a GST protein). A nucleic acid molecule encoding an HMGB polypeptide can be cloned into such an expression vector such that the fusion moiety is linked in-frame to the polypeptide.

HMGB functional equivalents can be generated using standard molecular biology techniques and assaying the function using, for example, methods described herein, such as, determining if the functional equivalent, when administered to a cell (e.g., a macrophage) increases release of a proinflammatory cytokine from the cell, compared to an untreated control cell.

HMGB polypeptides can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector introduced into a host cell and the polypeptide expressed in the host cell. The polypeptide can then be isolated from the cells by an appropriate purification scheme using standard protein purification techniques.

As used herein, an "HMGB A box" also referred to herein as an "A box" (and also known as HMG A box) is a protein or polypeptide that has one or more of the following biological activities: inhibiting inflammation mediated by HMGB and/or inhibiting release of a proinflammatory cytokine from a cell. In one embodiment, the HMGB A box polypeptide has one of the above biological activities. Typically, the HMGB A box polypeptide has both of the above biological activities. In one embodiment, the A box has at least 50%, 60%, 70%, 75%, 80%, 85%, 90%, or 95% sequence identity to SEQ ID NOs: 4 or 7. Preferably, the HMGB A box has no more than 10%, 20%, 25%, 30%, 40%, 50%, 60%, 70%, 80%, or 90% of the biological activity of full length HMGB. In one embodiment, the HMGB A box amino acid consists of the sequence of SEQ ID NO: 4 or SEQ ID NO: 7 (PTGKMSSYAFFVQTCREEHKKKHP-DASVNFSEFSKKCSER WKTMSAKEKGKFED-MAKADKARYEREMKTYIPPKGET) or the amino acid sequence in the corresponding region of an HMGB protein in a mammal. An HMGB A box is also a recombinantly produced polypeptide having the same amino acid sequence as the A box sequences described above. Preferably, the HMGB A box is a mammalian HMGB A box, for example, a human HMGB1 A box.

An HMGB A box often has no more than about 85 amino acids and no fewer than about 4 amino acids. Examples of polypeptides having A box sequences within them include, but are not limited to HMGB polypeptides described herein; GenBank Accession Numbers AAA64970, AAB08987, P07155, AAA20508, S29857, P09429, NP_002119, CAA31110, S02826, U00431, X67668, NP_005333, NM_016957, and J04197, mammalian HMG1 ((HMGB1) as described, for example, in GenBank Accession Number U51677), HMG2 ((HMGB2) as described, for example, in GenBank Accession Number M83665), HMG-2A ((HMGB3, HMG-4) as described, for example, in GenBank Accession Numbers NM_005342 and NP_005333), HMG14 (as described, for example, in GenBank Accession Number P05114), HMG17 (as described, for example, in GenBank Accession Number X13546), HMGI (as described, for example, in GenBank Accession Number L17131), and HMGY (as described, for example, in GenBank Accession Number M23618); nonmammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (Xenopus), HMG D (as described, for example, in GenBank Accession Number X71138) and HMG Z (as described, for example, in GenBank Accession Number X71139) (Drosophila); NHP10 protein (HMG protein homolog NHP 1) (as described, for example, in GenBank Accession Number Z48008) (yeast); non-histone chromosomal protein (as described, for example, in GenBank Accession Number O00479) (yeast); HMG 1/2 like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB00945 1), ste 11 (as described, for example, in GenBank Accession Number x53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ001183), SOX 12 (as described, for example, in GenBank Accession Number X73039) and SOX 21 (as described, for example, in GenBank Accession Number AF107044)); lymphoid specific factor (LEF-1) (as described, for example, in GenBank Accession Number X58636); T-cell specific transcription factor (TCF-1) (as described, for example, in GenBank Accession Number X59869); MTT1 (as described, for example, in GenBank Accession Number M62810) and SP100-HMG nuclear autoantigen (as described, for example, in GenBank Accession Number U36501).

Other examples of polypeptides having A box sequences within them include, but are not limited to polypeptides encoded by GenBank Accession Numbers NG_000897 (HMG1L10) (and in particular by nucleotides 658–1305 of NG_000897, as shown in FIGS. 7A and 7B); AF076674 (HMG1L1) (and in particular by nucleotides 1-633 of AF076674, as shown in FIGS. 7C and 7D; AF076676 (HMG1L4) (and in particular by nucleotides 1-564 of AF076676, as shown in FIGS. 7E and 7F); AC010149 (HMG sequence from BAC clone RP11-395A23) (and in particular by nucleotides 75503–76117 of AC010149), as shown in FIGS. 7G and 7H); AF165168 (HMG1L9) (and in particular by nucleotides 729–968 of AF 165168, as shown in FIGS. 7I and 7J); XM_063129 (LOC122441) (and in particular by nucleotides 319–558 of XM_063129, as shown in FIGS. 7K and 7L); XM_066789 (LOC139603) (and in particular by nucleotides 1-258 of XM_066789, as shown in FIGS. 7M and 7N); and AF165167 (HMG1L8) (and in particular by nucleotides 456–666 of AF165167, as shown in FIGS. 7O and 7P). The A box sequences in such polypeptides can be determined and isolated using methods described herein, for example, by sequence comparisons to A boxes described herein and testing for biological activity using methods described herein or other method known in the art.

Additional examples of HMGB A box polypeptide sequences include the following sequences: PDASVNFSEF SKKCSERWKT MSAKEKGKFE DMAKADKARY EREMKTYIPP KGET (human HMGB1; SEQ ID NO: 25); DSSVNFAEF SKKCSERWKT MSAKEKSKFE DMAKSDKARY DREMKNYVPP KGDK (human HMGB2; SEQ ID NO: 26); PEVPVNFAEF SKKCSERWKT VSGKEKSKFD EMAKADKVRY DREMKDYGPA KGGK (human HMGB3; SEQ ID NO: 27); PDASVNFSEF SKKCSERWKT MSAKEKGKFE DMAKADKARY EREMKTYIPP KGET (HMG1L10; SEQ ID NO: 28); SDASVNFSEF SNKCSERWKT MSAKEKGKFE DMAKADKTHY ERQMKTYIPP KGET (HMG1 L1; SEQ ID NO: 29); PDASVNFSEF SKKCSERWKA MSAKDKGKFE DMAKVDKADY EREMKTYIPP KGET (HMG1L4; SEQ ID NO: 30); PDASVKFSEF LKKCSETWKT IFAKEKGKFE DMAKADKAHY EREMKTYIPP KGEK (HMG sequence from BAC clone RP11-395A23; SEQ ID NO: 31); PDASINFSEF SQKCPETWKT TIAKEKGKFE DMAKADKAHY EREMKTYIPP KGET (HMGlL9; SEQ ID NO: 32); PDASVNSSEF SKKCSERWKTMPTKQGKFE DMAKADRAH (HMG1L8; SEQ ID NO: 33); PDASVNFSEF SKKCLVRGKT MSAKEKGQFE AMARADKARY EREMKTYIP PKGET (LOC122441; SEQ ID NO: 34); LDASVSFSEF SNKCSERWKT MSVKEKGKFE DMAKADKACY EREMKIYPYL KGRQ (LOC139603; SEQ ID NO: 35); and GKGDPKKPRG KMSSYAFFVQ TCREEHKKKH PDASVNFSEF SKKCSERWKT MSAKEKGKFE DMAKADKARY EREMKTYIPP KGET (human HMGB1 A box; SEQ ID NO: 36).

Functional equivalents of HMGB A boxes can also be used to carry out the methods of the present invention. Examples of HMGB A box functional equivalents include, for example, biologically active fragments, post-translational modifications, variants, or fusion proteins comprising A boxes, as defined herein. A box functional equivalents can be generated using standard molecular biology techniques and assaying the function using known methods, for example, by determining if the fragment, when administered to a cell (e.g., a macrophage) decreases or inhibits release of a proinflammatory cytokine from the cell.

Optionally, the HMGB A box polypeptide is a substantially pure, or substantially pure and isolated polypeptide that has been separated from components that naturally accompany it. Alternatively, the polypeptide may be in an unpurified form, for example, in a cell, cell milieu, or cell extract. The critical feature is that the preparation allows for the desired function of the polypeptide, even in the presence of considerable amounts of other components.

As used herein, an "HMGB B box" also referred to herein as a "B box" (and also known as an HMG B box) is a polypeptide that has at least 60%, 65%, 70%, 75%, 80%, 85%, 90%, or 95% sequence identity to SEQ ID NOs: 5 or 8 (as determined using the BLAST program and parameters described herein), lacks an A box, and has one or more of the following biological activities: increasing inflammation and/or increasing release of a proinflammatory cytokine from a cell. In one embodiment, the HMGB B box polypeptide has one of the above biological activities. Typically, the HMGB B box polypeptide has both of the above biological activities. Preferably, the HMGB B box has at least 25%, 30%, 40%, 50%, 60%, 70%, 80% or 90% of the biological activity of full length HMGB. In another embodiment, the HMGB box comprises or consists of the sequence of SEQ ID NO: 5 or SEQ ID NO: 8 (FKDPNAPKRLPSAFFLFCSEYRPKIKGEHPGLSIGDVAKKLGEMWNNTAADDK QPYEKKAAKLKEKYEKDIAAY) or the amino acid sequence in the corresponding region of an HMGB protein in a mammal.

Preferably, the HMGB B box is a mammalian HMGB B box, for example, a human HMGB1 B box. An HMGB B box often has no more than about 85 amino acids and no fewer than about 4 amino acids. Examples of polypeptides having B box sequences within them include, but are not limited to HMGB polypeptides described herein; GenBank Accession Numbers AAA64970, AAB08987, P07155, AAA20508, S29857, P09429, NP_002119, CAA31110, S02826, U00431, X67668, NP_005333, NM_016957, and J04197, mammalian HMG1 ((HMGB1) as described, for example, in GenBank Accession Number U51677), HMG2 ((HMGB2) as described, for example, in GenBank Accession Number M83665), HMG-2A ((HMGB3, HMG-4) as described, for example, in GenBank Accession Numbers NM_005342 and NP_005333), HMG14 (as described, for example, in GenBank Accession Number P05114), HMG17 (as described, for example, in GenBank Accession Number X13546), HMGI (as described, for example, in GenBank Accession Number L17131), and HMGY (as described, for example, in GenBank Accession Number M23618); non-mammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (Xenopus), HMG D (as described, for example, in GenBank Accession Number X71138) and HMG Z (as described, for example, in GenBank Accession Number X71139) (Drosophila); NHP10 protein (HMG protein homolog NHP 1) (as described, for example, in GenBank Accession Number Z48008) (yeast); non-histone chromosomal protein (as described, for example, in GenBank Accession Number O00479) (yeast); HMG 1/2 like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB00945 1), ste 11 (as described, for example, in GenBank Accession Number x53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ001183), SOX 12 (as described, for example, in GenBank Accession Number X73039) and SOX 21 (as described, for example, in GenBank Accession Number AF107044)); lymphoid specific factor (LEF-1) (as described, for example, in GenBank Accession Number X58636); T-cell specific transcription factor (TCF-1) (as described, for example, in GenBank Accession Number X59869); MTT1 (as described, for example, in GenBank Accession Number M62810); and SP100-HMGB nuclear autoantigen (as described, for example, in GenBank Accession Number U36501).

Other examples of polypeptides having B box sequences within them include, but are not limited to polypeptides encoded by GenBank Accession Numbers NG_000897 (HMG1L10) (and in particular by nucleotides 658-1305 of NG_000897, as shown in FIGS. 7A and 7B); AF076674 (HMG1L1) (and in particular by nucleotides 1-633 of AF076674, as shown in FIGS. 7C and 7D; AF076676 (HMG1L4) (and in particular by nucleotides 1-564 of AF076676, as shown in FIGS. 7E and 7F); AC010149 (HMG sequence from BAC clone RP1 1-395A23) (and in particular by nucleotides 75503–76117 of AC010149), as shown in FIGS. 7G and 7H) The B box sequences in such polypeptides can be determined and isolated using methods described herein, for example, by sequence comparisons to B boxes described herein and testing for biological activity.

Examples of HMGB B box polypeptide sequences include the following sequences: FKDPNAPKRP PSAFFLFCSE YRPKIKGEHP GLSIGDVAKK LGEMWNNTAA DDKQPYEKKA AKLKEKYEKD IAAY (human HMGB1; SEQ ID NO: 37); KKDPNAPKRP PSAFFLFCSE HRPKIKSEHP GLSIGDTAKK LGEMWSEQSA KDKQPYEQKA AKLKEKYEKD IAAY (human HMGB2; SEQ ID NO: 38); FKDPNAPKRL PSAFFLFCSE YRPKIKGEHP GLSIGDVAKK LGEMWNNTAA DDKQPYEKKA AKLKEKYEKD IAAY (HMG1L10; SEQ ID NO: 39); FKDPNAPKRP PSAFFLFCSE YHPKIKGEHP GLSIGDVAKK LGEMWNNTAA DDKQPGEKKA AKLKEKYEKD IAAY (HMG1L1; SEQ ID NO: 40); FKDSNAPKRP PSAFLLFCSE YCPKIKGEHP GLPISDVAKK LVEMWNNTFA DDKQLCEKKA AKLKEKYKKD TATY (HMG IL4; SEQ ID NO: 41); FKDPNAPKRP PSAFFLFCSE YRPKIKGEHP GLSIGDVVKK LAGMWNNTAA ADKQFYEKKA AKLKEKYKKD IAAY (HMG sequence from BAC clone RP11-359A23; SEQ ID NO: 42); and FKDPNAPKRP PSAFFLFCSE YRPKIKGEHP GLSIGDVAKK LGEMWNNTAA DDKQPYEKKA AKLKEKYEKD IAAYRAKGKP DAAKKGVVKA EK (human HMGB1 box; SEQ ID NO: 43).

Functional equivalents of HMGB B boxes can also be used to carry out the methods of the present invention. Examples of HMGB B box functional equivalents include, for example, biologically active fragments, post-translational modifications, variants, or fusion proteins comprising B boxes, as defined herein. B box functional equivalents can be generated using standard molecular biology techniques and assaying the function using known methods, for example, by determining if the fragment, when administered to a cell (e.g., a macrophage) increases release of a proinflammatory cytokine from the cell.

Optionally, the HMGB B box polypeptide is a substantially pure, or substantially pure and isolated polypeptide that has been separated from components that naturally accompany it. Alternatively, the polypeptide may be in an unpurified form, for example, in a cell, cell milieu, or cell extract. The critical feature is that the preparation allows for the desired function of the polypeptide, even in the presence of considerable amounts of other components.

HMGB polypeptides, HMGB A boxes, and HMGB B boxes, either naturally occurring or non-naturally occurring, include polypeptides that have sequence identity to the HMGB, HMGB A boxes, and HMGB B boxes described above. As used herein, two polypeptides (or a region of the polypeptides) are substantially homologous or identical when the amino acid sequences are at least about 60%, 70%, 75%, 80%, 85%, 90% or 95% or more homologous or identical. The percent identity of two amino acid sequences (or two nucleic acid sequences) can be determined by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). In certain embodiments, the length of the polypeptide aligned for comparison purposes is at least 30%, preferably, at least 40%, more preferably, at least 60%, and even more preferably, at least 70%, 80%, 90%, or 100% of the length of the reference sequence, for example, those sequences provided herein. The actual comparison of the two sequences can be accomplished by well-known methods, for example, using a mathematical algorithm. A preferred, non-limiting example of such a mathematical algorithm is described in Karlin et al., Proc. Natl. Acad. Sci. USA, 90:5873–5877 (1993). Such an algorithm is incorporated into the BLASTN and BLASTX programs (version 2.2) as described in Schaffer et al., Nucleic Acids Res., 29:2994–3005 (2001). When utilizing BLAST and Gapped BLAST programs, the default parameters of the respective programs (e.g., BLASTN) can be used. See, for example, the National Center for Biotechnology Information database. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, Comput. Appl. Biosci., 10:3–5 (1994); and FASTA described in Pearson and Lipman, Proc. Natl. Acad. Sci. USA, 85:2444–8 (1988).

In another embodiment, the percent identity between two amino acid sequences can be accomplished using the GAP program in the GCG software package (Accelrys, Inc., San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys, San Diego, Calif.), using a gap weight of 50 and a length weight of 3.

As used herein, a Toll-like receptor 2 (TLR2) protein is a polypeptide that can bind an HMGB protein and mediate inflammation and/or release of a pro-inflammatory cytokine from a cell and has at least 50%, 60%, 70%, 75%, 80%, 85%, 90% or 95% sequence identity of SEQ ID NO: 46 (GenBank Accession Number AAC34133). In one embodiment the TLR2 is mammalian, for example, human. In another embodiment, the TLR2 comprises or consists of the amino acid sequence of SEQ ID NO: 46. In still another embodiment, the TLR2 protein is encoded by the nucleic acid sequence of SEQ ID NO: 47 (GenBank Accession number U88878). Optionally, the TLR2 protein is a substantially pure, or substantially pure and isolated polypeptide that has been separated from components that naturally accompany it, or a recombinantly produced polypeptide having the same amino acid sequence. Alternatively, the TLR2 protein may be in an unpurified form, for example, in a cell (intracellular), a plasma membrane (on the surface of a cell or in a vesicle (e.g., an endosome), or a cell extract. TLR2 proteins also include functional equivalents of TLR2, for example, biologically active fragments, post-translational modifications, or variants, as defined herein.

As used herein, a "cytokine" is a protein or peptide that is naturally produced by mammalian cells and that acts in vivo as a regulator at micro- to picomolar concentrations. Cytokines can, either under normal or pathological conditions, modulate the functional activities of individual cells and tissues. A proinflammatory cytokine is a cytokine that is capable of causing (directly or indirectly) a physiological reaction associated with inflammation, for example, vasodilation, hyperemia, increased permeability of vessels with associated edema, accumulation of granulocytes and mononuclear phagocytes, or deposition of fibrin. In some cases, the proinflammatory cytokine can also cause apoptosis, such as in chronic heart failure, where TNF has been shown to stimulate cardiomyocyte apoptosis (Pulkki, Ann. Med. 29:339–343 (1997); and Tsutsui et al., Immunol. Rev. 174: 192–209 (2000)).

Nonlimiting examples of proinflammatory cytokines are tumor necrosis factor (TNF), interleukin (IL)-1α, IL-1β, IL-6, IL-8, IL-18, interferon γ, HMG-1 (also know as HMG1, and HMGB1), and macrophage migration inhibitory factor (MIF).

Proinflammatory cytokines are to be distinguished from anti-inflammatory cytokines, such as IL-4, IL-10, and IL-13, which are not mediators of inflammation.

In many instances, proinflammatory cytokines are produced in an inflammatory cytokine cascade, defined herein as an in vivo release of at least one proinflammatory cytokine in a mammal, wherein the cytokine release affects a physiological condition of the mammal. Thus, an inflammatory cytokine cascade is inhibited in embodiments of the invention where proinflammatory cytokine release causes a deleterious physiological condition.

When referring to the effect of any of the compositions or methods of the invention on the release of proinflammatory cytokines, the use of the terms "inhibit" or "decrease" encompasses at least a small but measurable reduction in proinflammatory cytokine release. In preferred embodiments, the release of the proinflammatory cytokine is inhibited by at least 20% over non-treated controls; in more preferred embodiments, the inhibition is at least 50%; in still more preferred embodiments, the inhibition is at least 70%, and in the most preferred embodiments, the inhibition is at least 80%. Such reductions in proinflammatory cytokine release are capable of reducing the deleterious effects of an inflammatory cytokine cascade in in vivo embodiments.

Agents that Inhibit the Interaction between HMGB and TLR2

The present invention provides screening methods for identifying agents (inhibitors) that inhibit the interaction (e.g., binding) between HMGB and TLR2. The agents can be used in therapeutic methods as described herein. As used herein, an "inhibitor" is an agent that acts by inhibiting (preventing or decreasing) at least one function characteristic of the interaction between an HMGB protein and a TLR2, such as a binding activity (complex formation), cellular signaling triggered by the interaction and/or cellular response function (e.g., an inflammatory response, release of a proinflammatory cytokine from a cell) mediated by the interaction.

As used herein, the term inhibitor includes agents that bind to TLR2 and prevents binding thereto by HMGB. In one embodiment the agent binds TLR2 (e.g., an antibody or antigen-binding fragment, a mutant of a natural ligand, a peptidomimetic, and other competitive inhibitors of ligand binding) and inhibits binding by HMGB. In one embodiment, the agent is a ligand that binds to TLR2 with greater affinity than HMGB binds to TLR2. Preferably the agent that binds to TLR2, thereby inhibiting binding by HMGB, does not significantly initiate or increase an inflammatory response, or does not significantly initiate or increase the release of a proinflammatory cytokine from a cell.

Examples of ligands that are known to bind TLR2 include: heat shock protein 60, surfactant protein-A, monophosphoryl lipid A (Botler et al., Infect. Immun. 71(5): 2498–2507 (2003)), muramyl dipeptide (Beutler et al., Blood Cells Mol. Dis. 27(4):728–730 (2001)), yeast-particle zymosan, GPI anchor from *Trypanosoma cruzi*, *Listeria monocytogenes*, *Bacillus*, lipoteichoic acid, peptidoglycan, and lipopeptides from *Streptococcus* species, heat killed *Mycobacteriua tuberculosis*, *Mycobacteria avium* lipopeptide, lipoarabinomannan, mannosylated phosphatidylinositol, *Borrelia burgdorferi*, *Treponemapallidum*, *Treponema maltophilum* (lipopeptides, glycolipids, outer surface protein A), and MALP-2 lipopeptides from *Mycoplasma fermentans*. Therefore, these molecules, as well as portions of these molecules that bind TLR2 can be used to inhibit the interaction between HMGB and TLR2. It is also reasonable to believe that another ligand for TLR2 is the HMGB A box and TLR2 binding fragments thereof (see, for example, U.S.

application Ser. No. 10/147,447, the entire teaching of which are incorporated herein by reference).

In another embodiment, the inhibitor binds HMGB, and prevents HMGB from binding to TLR2. Such an agent can be, for example, a soluble form of recombinant TLR2 (sTLR2) (i.e., TLR2 lacking the intracellular and transmembrane domains, as described, for example, by Iwaki et al., Journal of Biological Chemistry 277(27):24315–24320 (2002)) or an non-HMG1 antibody molecule (e.g., a protein, peptide, or non-peptidic small molecule) that binds HMG1 and prevents it from binding to TLR2. The sTLR2 molecule can contain the extracellular domain (for example, amino acids 1-587 of the TLR2 amino acid sequence (e.g., GenBank Accession Number). The sTLR molecule can also be modified with one of more amino acid substitutions and/or post-translational modifications provided such sTLR2 molecules have HMGB binding activity, which can be assessed using methods known in the art. Such sTLR2 molecules can be made, for example, using recombinant techniques. Preferably the sTLR2 has at least 70%, 75%, 80%, 85%, 90%, or 95% to amino acids 1-587 of GenBank Accession Number AAC34133. In another embodiment, the inhibitor is an agent that bind TLR2 a site different than the HMGB binding site and blocks binding by HMGB (e.g., by causing a conformation change in the TLR2 protein or otherwise altering the binding site for HMGB).

In one embodiment, the inhibitor is not an anti-TLR2 antibody or antigen-binding fragment thereof. In another embodiment, the inhibitor is not an antibody that binds HMGB1 (an anti-HMGB1 antibody) or an antigen-binding fragment thereof. In another embodiment, the inhibitor is not an antibody that binds HMGB (an anti-HMGB antibody) or an antigen-binding fragment thereof. In another embodiment, the inhibitor is not soluble RAGE (i.e., a portion of the RAGE receptor that binds HMGB1). In another embodiment, the inhibitor is non-microbial (i.e., is not a microbe, derived from a microbe, or secreted or released from a microbe). In still another embodiment, the inhibitor is a mammalian inhibitor (i.e., is a molecule that naturally exists in a mammal, is derived from a molecule that naturally exists in a mammal, or is secreted or released from a mammalian cell), for example, a human inhibitor. Preferably, the inhibitor inhibits the interaction between HMGB and TLR2 by at least about 10%, 25%, 50%, 60%, 70%, 80%, 90% or 100% compared to a suitable control (e.g., a sample receiving no inhibitor or receiving the inhibitor vehicle only). In another embodiment, the inhibitor is a small molecule inhibitor (i.e., having a molecular weight of 1000 or less, 500 or less, 250 or less or 100 or less). In another embodiment the inhibitor is a short peptide, having, for example, 50 or fewer amino acids, 30 or fewer amino acids, 25 or fewer amino acids, 20 or fewer amino acids, 10 or fewer amino acids, or 5 or fewer amino acids. In another embodiment, the inhibitor is not an HMGB A box. In another embodiment the inhibitor is not a peptide. In another embodiment, the inhibitor inhibits the interaction between HMGB and TLR2 at a level useful in vivo, such that the dose can be tolerated by an individual and would be useful to an individual. Preferably the activity of the inhibitor is such that less than 1 g, less than 100 mg, less than 10 mg, less than 1 mg, less than 100 μg, less than 10 μg, less than 1 μg, less than 100 ng, less than 10 ng, or less than 1 ng of the inhibitor is used in the assays and/or therapeutic methods described herein or comparable assays or methods.

Antibodies

In one embodiment, the inhibitor is an antibody or an antigen-binding fragment of an antibody. The term "antibody" as used herein refers to immunoglobulin molecules and immunologically active portions of immunoglobulin molecules, i.e., molecules that contain an antigen binding site that selectively binds an antigen (e.g., an antigen-binding fragment of an antibody). The antibodies of the present invention are molecules that selectively bind to a TLR2 or functional equivalent thereof (e.g., a fragment thereof). In a preferred embodiment, the antibodies do not substantially bind other molecules in a sample. Preferably, the antibody is at least 60%, by weight, free from proteins and naturally occurring organic molecules with which it naturally associated. More preferably, the antibody preparation is at least 75% or 90%, and most preferably, 99%, by weight, antibody.

The antibodies of the present invention can be polyclonal or monoclonal, and the term antibody is intended to encompass both polyclonal and monoclonal antibodies. The terms polyclonal and monoclonal refer to the degree of homogeneity of an antibody preparation, and are not intended to be limited to particular methods of production.

Antibodies of the present invention can be raised against an appropriate immunogen, including proteins or polypeptides of TLR2 described herein (including synthetic molecules, such as synthetic peptides).

Preparation of immunizing antigen, and polyclonal and monoclonal antibody production can be performed using any suitable technique. A variety of methods have been described (see e.g., Kohler et al., Nature, 256:495–497 (1975)) and Eur. J. Immunol. 6:511–519 (1976)); Milstein et al., Nature 266:550–552 (1977)); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); and Current Protocols In Molecular Biology, Vol. 2 (Supplement 27, Summer '94), Ausubel, F. M. et al., Eds., (John Wiley & Sons: New York, N.Y.), Chapter 11, 1991); the teachings of each of which are incorporated herein by reference). Generally, a hybridoma is produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies (see e.g., Jakobovits et al., Proc. Natl. Acad. Sci. USA, 90:2551–2555 (1993)); Jakobovits et al., Nature, 362:255–258 (1993)); Lonberg et al., U.S. Pat. No. 5,545,806; and Surani et al., U.S. Pat. No. 5,545,807; the teachings of which are each incorporated herein by reference).

Single-chain antibodies, and chimeric, humanized or primatized (CDR-grafted), or veneered antibodies, as well as chimeric, CDR-grafted or veneered single-chain antibodies, comprising portions derived from different species, and the like are also encompassed by the present invention and the term "antibody." The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan et al., EP 0 519 596 A1. See also, Newman et al., BioTechnology, 10:1455–1460 (1992), regarding primatized antibody, and Ladner et al., U.S. Pat. No. 4,946,778 and Bird et al., Science, 242: 423–426 (1988) regarding single-chain antibodies.

In addition, antigen-binding fragments of antibodies, including fragments of chimeric, humanized, primatized, veneered or single-chain antibodies, can also be produced. In one embodiment, the antigen-binding fragment is a soluble TLR2 molecule(e.g., an extracellular TLR2 domain as described, for example, by Iwaki et al., supra). Antigen-binding fragments of foregoing antibodies retain at least one binding function and/or modulation function of the full-length antibody from which they are derived. For example, antigen-binding fragments capable of binding to a TLR2 or a functional variant thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Reduction of the disulfide bond between the heavy chains of F(ab')$_2$ fragments can yield F(ab') fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH, domain and hinge region of the heavy chain.

The antibodies and fragments of the present invention can be modified, for example, by incorporation of or attachment (directly or indirectly) of a detectable label. Examples of detectable labels include various spin labels, antigen or epitope tags, haptens, enzyme labels, prosthetic groups, fluorescent materials, chemiluminescent materials, bioluminescent materials, and radioactive materials. Examples of suitable enzyme labels include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a chemiluminescent material includes luminol; examples of bioluminescent materials include luciferase, luciferin, and aequorin, and examples of suitable radioactive material include $^{125}$I, $^{131}$I, $^{35}$S, and $^3$H.

Aptamers

In one embodiment, the agent that inhibits interaction between HMGB and TLR2 is an aptamer. Aptamers are single stranded oligonucleotides or oligonucleotide analogs that bind to a particular target molecule, such as a protein or a small molecule (e.g., a steroid or a drug, etc.). Thus, aptamers are the oligonucleotide analogy to antibodies. However, aptamers are smaller than antibodies, generally in the range of 50–100 nucleotides. Their binding is highly dependent on the secondary structure formed by the aptamer oligonucleotide. Both RNA and single stranded DNA (or analog), aptamers are known. See, e.g., Burke et al., J. Mol. Biol. 264:650 (1996); Ellington and Szostak, Nature 346: 818 (1990); Hirao et al., Mol. Divers. 4:75 (1998); Jaeger et al., The EMBO Journal 17:4535 (1998); Kensch et al., J. Biol. Chem. 275:18271 (2000); Schneider et al., Biochemistry 34:9599 (1995); and U.S. Pat. Nos. 5,773,598; 5,496, 938; 5,580,737; 5,654,151; 5,726,017; 5,786,462; 5,503, 978; 6,028,186; 6,110,900; 6,124,449; 6,127,119; 6,140, 490; 6,147,204; 6,168,778; and 6,171,795. Aptamers can also be expressed from a transfected vector (Joshi et al., J. Virol. 76:6545 (2002).

Aptamers that bind to a particular target, for example, TRL2 or HMGB, can be selected by using an iterative process called SELEX, which stands for Systematic Evolution of Ligands by EXponential enrichment (Burke et al., supra; Ellington and Szostak, supra; Schneider et al., supra; Tuerk and Gold, Proc. Natl. Acad. Sci. USA 89:6988 (1992); and Tuerk and Gold, Science 249:505 (1990)). Several variations of SELEX have been developed, which improve the process and allow its use under particular circumstances. See, e.g., U.S. Pat. Nos. 5,472,841; 5,503,978; 5,567,588; 5,582,981; 5,637,459; 5,683,867; 5,705,337; 5,712,375; and 6,083,696. Thus, the production of aptamers to a particular oligopeptide, including TLR2 or HMGB, requires no undue experimentation. Screening Methods for Identifying Agents that Inhibit the Interaction Between HMGB and TLR2

The present invention provides assays for screening candidate inhibitors or test agents (e.g., a candidate compound) to detect and/or identify those that inhibit at least one function characteristic of the interaction between a HMGB and TLR2, as described herein, as well as agents identifiable by the assays. As used herein, a "candidate inhibitor" or "test agent" is a molecule, be it naturally-occurring or artificially-derived, and includes, for example, peptides, proteins, peptidomimetics, synthetic molecules, for example, synthetic organic molecules, naturally-occurring molecules, for example, naturally occurring organic molecules, nucleic acid molecules, and components thereof.

In general, test agents for use in the present invention may be identified from libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic small molecule libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In addition, natural and synthetically produced molecules or libraries can be generated by any suitable method (e.g., by standard extraction and fractionation methods). For example, candidate compounds can be obtained using any of the numerous approaches in combinatorial library methods, including biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des., 12:145 (1997)). Furthermore, if desired, any library or compound can be readily modified using standard chemical, physical, or biochemical methods.

It is understood that an inhibitor can inhibit a function characteristic of the interaction between HMGB and TLR2 in varying degrees. For example, the inhibitor can decrease the function characteristic of the interaction between HMGB and TLR2 by at least about 10%, 20%, 40%, 50%, or 75%, or by at least about 90%, relative to an appropriate control.

When a crude extract is found to inhibit a function characteristic of the interaction between HMGB and TLR2, further fractionation of the positive lead extract can be performed to isolate chemical constituents responsible for the observed effect. The assays described herein for the detection and/or identification of activities in mixtures of compounds can be used to purify the active component or to test derivatives thereof. If desired, compounds shown to be useful agents for treatment can be chemically modified according to methods known in the art. Compounds identified as being of therapeutic value may be subsequently analyzed using animal models for diseases in which it is desirable to alter a function characteristic of the interaction between HMGB and TLR2.

Binding Inhibition Assays

Binding inhibition assays can be carried out using any suitable method. Such assays can be used, alone or in combination with each other or other suitable methods, to identify inhibitors of a function characteristic of the interaction between HMGB and TLR2 (e.g., an anti-inflammatory agent). The methods of the present invention can be adapted for high-throughput screening in which large numbers of samples are processed (e.g., a 96- or 384-well format). Such assays can be carried out using cells (for example, macrophages), cell extracts, or purified proteins.

Binding inhibition assays can be used to identify agents that inhibit the interaction between HMGB and TLR2. For example, a binding assay can be conducted in which the binding of HMGB to TLR2 in the absence of a candidate inhibitor, is compared with the binding of HMGB to TLR2 in the presence of the candidate inhibitor. TLR2 can be contacted with HMGB ligand and the candidate inhibitor simultaneously, or one after the other, in either order. A reduction in the extent of binding of HMGB to TLR2 in the presence of the candidate inhibitor is indicative that the candidate is an inhibitor.

In one method for detection and/or identification of inhibitors, an agent (e.g., a composition comprising one or more candidate inhibitors) to be tested, TLR2 and HMGB can be maintained under conditions suitable for binding, and formation of a complex between the HMGB and TLR2 is detected or measured. For example, the extent of complex formation can be determined relative to a suitable control (e.g., compared with background determined in the absence of the candidate inhibitor, or compared with complex formation with a second agent (i.e., a standard)).

An interaction (e.g., complex formation) between HMGB and TLR2 can be detected directly (for example, by measuring the binding affinity, using standard methods. In one embodiment, the TLR2, candidate inhibitor, or the HMGB can be labeled with a suitable label (e.g., fluorescent moiety, chemiluminescent group, epitope tag, radioisotope, enzyme label, or affinity tag), and complex formation can be determined indirectly by detection of the label. Specificity of binding can be assessed by competition or displacement, for example, using a known TLR2 or HMGB ligand (e.g., those described herein) as a competitor.

In another example, a fusion protein comprising HMGB and a detectable label, for example, a fluorescent protein, such as green fluorescent protein, or a hapten that can be detected with an antibody (e.g., labeled antibody), such as glutathione S-transferase or biotin is contacted with TLR2. The TLR2 can be immobilized on a solid support, for example, a microtiter well. Preferably, the TLR2 and fusion protein are in a solution suitable for complex formation between TLR2 and HMGB, as described herein. The fusion protein binds to TLR2. Unbound fusion protein can be removed, for example, by washing the solid support or by other means suitable for separation of unbound fusion protein from bound fusion protein complexed with TLR2. The complex formed between the fusion protein and TLR2 is then indirectly detected, for example, by measuring fluorescence of bound fluorescent protein, or by contacting the complex with an antibody that binds the hapten portion of the fusion protein, using, for example, an ELISA assay or a radioimmunoassay. The assay can be repeated in the presence of a candidate inhibitor. If the candidate inhibitor disrupts complex formation between the TLR2 binding fusion protein and TLR2, then a decrease in the signal can be detected due to decreased complex formation between the fusion protein and TLR2. Such a decrease indicates that the candidate inhibitor is an inhibitor of the ineraction between HMGB and TLR2. Alternatively, the HMGB fusion polypeptide can be immobilized on a solid support, and the TLR2 and candidate inhibitor is added and assessed for complex formation.

In another example, a fusion protein comprising HMGB and an enzyme, for example, β-galactosidase, luciferase, chloramphenicol acetyl transferase, or alkaline phosphatase, is contacted with TLR2. The TLR2 can be immobilized on a solid support, for example, a microtiter well. Preferably, the TLR2 and fusion protein are in a solution suitable for complex formation between TLR2 and HMGB, as described herein. The fusion protein will bind to TLR2. Unbound fusion protein can be removed, for example, by washing the solid support or by other means suitable for separation of unbound fusion protein from bound fusion protein complexed with TLR2. The complex formed between the fusion protein and TLR2 can be indirectly detected, for example, by adding the appropriate substrate for the enzyme present in the fusion protein, and detecting enzyme activity using, for example, using a microplate reader or a luminometer. The assay can be repeated in the presence of a candidate inhibitor. If the candidate inhibitor disrupts complex formation between the fusion protein and TLR2, then a decrease in enzyme activity due to decreased complex formation between the fusion protein and TLR2 can be detected. Such a decrease indicates that the candidate inhibitor is an inhibitor of TLR2 binding.

Another method for identifying an inhibitor of the interaction between HMGB and TLR2 is through phage display techniques. For example, HMGB can be expressed on the surface of phage (e.g., as a fusion protein with a phage coat protein). The phage is then contacted with TLR2 (immobilized, for example, on a solid support, such as a microtiter well) and the phage binds to the TLR2. The complex can be detected using any suitable method. For example, the complex can be contacted with an antibody that recognizes the phage, and binding of the antibody can be detected using, for example, an ELISA assay or a radioimmunoassay. The assay can be repeated in the presence of a candidate inhibitor. If the candidate inhibitor disrupts complex formation between the HMGB displayed on the phage, then a decrease in signal (e.g., the amount of antibody binding) can be detected due to decreased complex formation between the fusion and TLR2. Such a decrease indicates that the candidate inhibitor is an inhibitor of TLR2 binding.

Cell based assays can also be used to detect and/or identify inhibitors of the interaction between HMGB and TLR2. For example, a yeast two-hybrid system such as that described by Fields and Song (Fields and Song, Nature 340:245–246 (1989)) can be used to identify polypeptides that interact with TLR2. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used that includes a nucleic acid encoding a DNA binding domain and a TL2 receptor polypeptide or an HMGB polypeptide, or functional equivalent or derivative thereof, and a second vector is used that includes a nucleic acid encoding a transcription activation domain and a nucleic acid encoding a polypeptide that potentially may interact with the TLR2 polypeptide or HMGB polypeptide of interest, or functional equivalent or derivative thereof. Incubation of yeast containing the first vector and the second vector under appropriate conditions (e.g., mating conditions such as used in the MATCHMAKER™ system from Clontech) allows identification of colonies that express the markers of the polypeptide(s). These colonies can be examined to identify the polypeptide(s) that interact with the TLR2 polypeptide or HMGB polypeptide encoded by the nucleic acid molecule or a functional equivalent or derivative thereof. Such polypeptides may be useful as compounds that bind to HMGB or TLR2 and inhibit the interaction between TLR2 and HMGB and can be further tested using, for example, assays described herein.

Inhibitors of the interaction between HMGB and TLR2 can also be identified by measuring release of a proinflammatory cytokine from a cell, for example, a macrophage, or MyD 88 activity or NF-κB activity in an ex vivo assay. For example, an interaction between HMGB and TLR2 results in the release of proinflammatory cytokines from the cell, which can be detected and measured using, for example, ELISA kits. MyD 88 or NF-κB activity can be assessed as described herein, using commercially available kits, or using other methods known to one skilled in the art. The assay can be repeated in the presence of a candidate inhibitor. If the candidate inhibitor disrupts the interaction between the HMGB and TLR2, then a decrease in cytokine release, MyD 88, activity, or NF-κB activity can be detected due to decreased interaction between HMGB and TLR2. Such a decrease indicates that the candidate inhibitor is an inhibitor of the interaction of HMGB with TLR2.

In certain embodiments it may be desirable to immobilize (directly or indirectly) a component of the assay on a matrix or other solid support, in order to facilitate separation of bound from unbound components of the assay, as well as to accommodate automation of the assay. The above-described assays can be carried out in any suitable manner for combining the reactants. For example, the components may be combined in a suitable vessel such as a microtiter plate, test tube, or micro-centrifuge tube. In one embodiment, a fusion protein (e.g., a glutathione-S-transferase fusion protein) can be provided that adds a domain that allows a component of the assay to be bound to a matrix or other solid support.

Detection and/or identification of an inhibitor of complex formation between a HMGB and TLR2 can also occur through the use of "in silico" screening methods, which involve the use of computer programs to test the docking of candidate inhibitors. Such methods comprise determining functional residues of HMGB involved in forming a complex with TLR2; developing one or more three-dimensional structures based on the functional residues identified in the previous step using any suitable method; comparing the one or more three-dimensional structures with one or more test agents having calculatable tertiary structures; and identifying agents having a spatial orientation consistent with forming a complex with TLR2 and inhibiting complex formation between TLR2 and HMGB. Agents identified in this manner can be further assessed for activity using, for example, assays described herein, and can be used as anti-inflammatory agents.

Information regarding the HMGB functional residues involved in forming a complex with TLR2 can be used to develop one or more three-dimensional structures with which a successful test agent (i.e., an inhibitor of the interaction between HMGB and TLR2) comes into contact with TLR2. The three-dimensional structures are compared with or tested against one or more test agents that have calculatable tertiary structures. For example, computer programs in which one or more test agents are individually docked to TLR2 and examined for suitable spatial orientation with respect to the TLR2 can be used to test for an appropriate test agent. A test agent has suitable spatial orientation if the test agent binds to TLR2 with favorable energy, as determined using the parameters of the computer software used to detect docking of test agents and associated binding energies. Successful compounds, or derivatives thereof can then be tested using in vitro or in vivo assays, for example, as described herein.

This invention further pertains to novel compounds identified by the above-described screening assays. Accordingly, it is within the scope of this invention to further use an agent identified as described herein in an appropriate animal model. For example, a compound identified as described herein (e.g., a candidate compound that is an inhibitor of complex formation between a HMGB and TLR2) can be used in an animal model to determine the efficacy, toxicity, or side effects of treatment with such a compound, for example, as described below.

Pharmaceutical Compositions

The present invention is also directed to a composition comprising an agent that inhibits the interaction of HMGB and TLR2 in a pharmaceutically acceptable carrier. Preferably, the agent binds to TLR2 and inhibits binding by HMGB. Thus, the composition and methods disclosed herein can be used to inhibit an inflammatory condition. The condition can be one where the inflammatory cytokine cascade causes a systemic reaction, such as with endotoxic shock. Alternatively, the condition can be mediated by a localized inflammatory cytokine cascade, as in rheumatoid arthritis. Preferably, the inflammatory condition is appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion ischemia, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, bums, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, chronic obstructive pulmonary disease, psoriasis, allograft rejection, graft-versus-host disease, Type I diabetes, ankylosing spondylitis, Berger's disease, Retier's syndrome, or Hodgkins disease. In one embodiment, the condition is not sepsis. In another embodiment, the condition is not a bacterial infection or bacterial sepsis. In another embodiment, the condition is not septic shock, rosecea, acne, shock, a viral infection, toxic shock, acute inflammation, chronic inflammation, atopic dermatitis, chronic obstructive pulmonary disease, or intestinal inflammation.

In more preferred embodiments, the condition is peritonitis, pancreatitis, ulcerative colitis, Crohn's disease, organ ischemia, reperfusion ischemia, cachexia, bums, myocardial ischemia, adult respiratory distress syndrome, multiple sclerosis, restenosis, rheumatoid arthritis, systemic lupus erythematosus, Behcet's syndrome, psoriasis, allograft rejection and graft-versus-host disease. Where the condition is allograft rejection, the composition may advantageously also include an immunosuppressant that is used to inhibit allograft rejection, such as cyclosporin.

The carrier included with the polypeptide in these compositions is chosen based on the expected route of administration of the composition in therapeutic applications. The route of administration of the composition depends on the condition to be treated. For example, intravenous injection may be preferred for treatment of a systemic disorder such as endotoxic shock, and oral administration may be preferred to treat a gastrointestinal disorder such as a gastric ulcer. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the antibody composition can be administered orally, parenterally, intranasally, vaginally, rectally, lingually, sublingually, bucally, intrabuccaly, and transdermally to the patient.

Accordingly, compositions designed for oral, lingual, sublingual, buccal, and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with carriers and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth, or gelatin. Examples of carriers include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various compositions should be pharmaceutically pure and non-toxic in the amounts used.

Methods of Therapy

Inhibition of the binding of HMGB to TLR2 according to the present invention, provides an effective way of inhibiting TLR2-binding-mediated functions, for example, inflammation and/or release of a proinflammatory cytokine from a cell. Thus, agents that inhibit the interaction between TLR2 and HMGB, including inhibitors such as those identified as described herein, can be used as agents to treat inflammatory conditions, for therapeutic purposes.

The route of administration and the dosage of the agent or pharmaceutical composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Typically, an effective amount can range from 0.01 mg per day to about 100 mg per day for an adult. Preferably, the dosage ranges from about 1 mg per day to about 100 mg per day or from about 1 mg per day to about 10 mg per day.

In one aspect, the present invention provides a method of treating an inflammatory condition in an individual, or treating an individual at risk for having an inflammatory condition, comprising administering to the individual an effective amount of an agent that inhibits the interaction between HMGB and TLR2 to an individual in need of such therapy. In one embodiment, the agent binds TLR2 and inhibits binding by HMGB. As used herein, an "effective amount" is an amount sufficient to prevent or decrease an inflammatory response, or to improve an inflammatory condition. Methods for assessing inflammatory responses and conditions are known in the art.

The terms "therapeutic" and "treatment" as used herein, refer to ameliorating symptoms associated with a disease or condition, including preventing or delaying the onset of the disease symptoms, and/or lessening the severity or frequency of symptoms of the disease or condition. The term "individual" is defined herein to include animals such as mammals, including, but not limited to, primates, cows, sheep, goats, horses, dogs, cats, rabbits, guinea pigs, rats, mice or other bovine, ovine, equine, canine, feline, rodent, or murine species. In one embodiment, the animal is a human. Diseases and conditions associated with inflammation can be treated using the method.

Inflammatory diseases or conditions that can be treated with inhibitors of the binding of HMGB to TLR2 are described herein.

Modes of Administration

The pharmaceutical compositions of the present invention can be administered parenterally such as, for example, by intravenous, intramuscular, intrathecal, or subcutaneous injection. Parenteral administration can be accomplished by incorporating the antibody compositions of the present invention into a solution or suspension. Such solutions or suspensions may also include sterile diluents such as water for injection, saline solution, fixed oils, polyethylene glycols, glycerine, propylene glycol, or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes, or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the antibody composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves, and the like.

The present invention includes nasally administering to the mammal a therapeutically effective amount of the pharmaceutical composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the agonist prepared by well-known methods to be administered, for example, as a nasal spray, nasal drop, suspension, gel, ointment, cream, or powder. Administration of the composition may also take place using a nasal tampon or nasal sponge.

The therapeutic compositions described herein can also include an antagonist of an early sepsis mediator. As used herein, an early sepsis mediator is a proinflammatory cytokine that is released from cells soon (i.e., within 30–60 min.) after induction of an inflammatory cytokine cascade (e.g., exposure to LPS). Nonlimiting examples of these cytokines are TNF, IL-1α, IL-1β, IL-6, PAF, and MIF. Also included as early sepsis mediators are receptors for these cytokines (for example, tumor necrosis factor receptor type 1) and enzymes required for production of these cytokines, for example, interleukin-1β converting enzyme). Antagonists of any early sepsis mediator, now known or later discovered, can be useful for these embodiments by further inhibiting an inflammatory cytokine cascade.

Exemplification

Figure 1A:
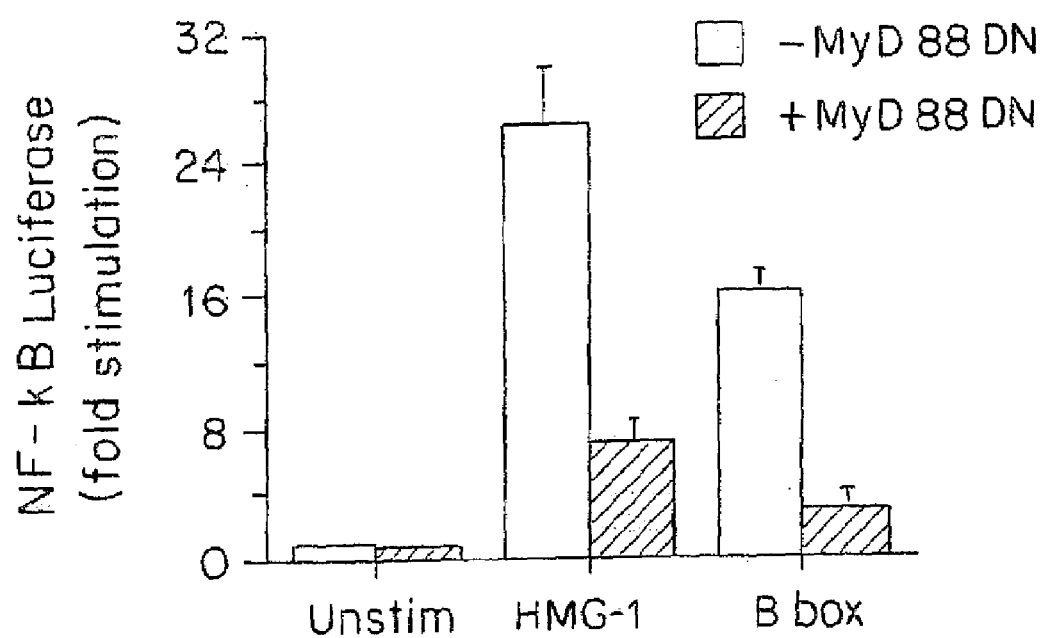
FIG. 1A is a histogram of the effect of HMG1 or HMG1 B box polypeptide stimulation on activation of the NF-κB-dependent ELAM promoter (measured by luciferase activity) in RAW 264.7 cells co-transfected with a murine MyD 88-dominant negative (+MyD 88 DN) mutant (corresponding to amino acids 146-296), or empty vector (−MyD 88 DN). Data are expressed as the ratio (fold-activation) of average luciferase values from unstimulated and stimulated cells (subtracted for background)+SD.

To examine the effects of HMGB1 or HMGB1 B Box on the NF-κB-dependent ELAM promoter, the following experiment was carried out. RAW 264.7 macrophages were transiently co-transfected with an expression plasmid encoding a murine MyD 88-dominant-negative (DN) mutant (corresponding to amino acids 146–296), or empty vector, plus a luciferase reporter plasmid under the control of the NF-κB-dependent ELAM promoter, as described by Means et al. (J. Immunol. 166:4074–4082 (2001)). A portion of the cells were then stimulated with full-length HMBG1 (100 ng/ml), or purified HMGB1 B box (10 µg/ml), for 5 hours. Cells were then harvested and luciferase activity was measured, using standard methods. All transfections were performed in triplicate, repeated at least three times, and a single representative experiment is shown in FIG. 1A. As shown in FIG. 1A, HMGB1 stimulated luciferase activity in samples that were not co-transfected with the MyD 88 dominant negative, and the level of stimulation was decreased in samples that were co-transfected with the MyD 88 dominant negative. This effect was also observed in samples administered HMGB B box.

Figure 1B:
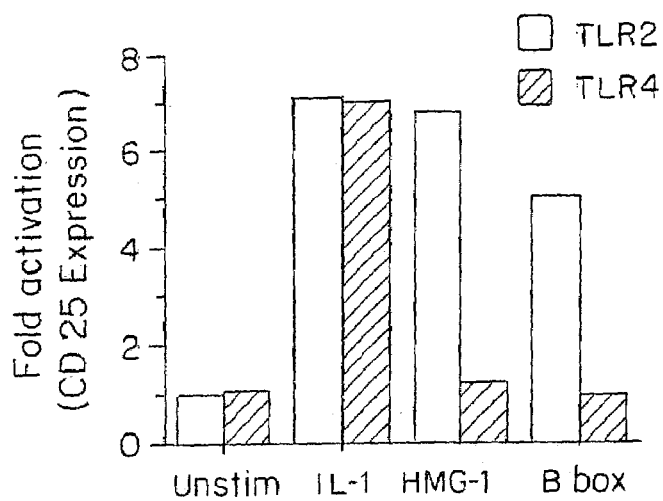
FIG. 1B is a histogram of the effect of stimulation of CHO reporter cell lines that constitutively express human TLR2 (open bars) or TLR4 (shaded bars) with IL-1, HMG1, or HMG1 B box on CD25 expression. Data are expressed as the ratio (fold-activation) of the percent of $CD25^+$ cells in unstimulated and stimulated cell populations that were gated to exclude the lowest 5% of cells based on mean FL1 fluorescence.

The effect of HMGB1 or HMGB1 B box on NF-κB activation was also examined. CHO reporter cell lines that constitutively express human Toll-like receptor 2 (TLR2) or Toll-like receptor 4 (TLR4) have been previously described (Means et al., J. Immunology, 163:3920–3927 (1999)). These reporter lines also contain a stably transfected ELAM-CD25 reporter gene, and express human CD25 on their surface as a consequence of NF-κB activation. CHO/TLR2 and CHO/TLR4 cells were stimulated with IL-1 (10 ng/ml), purified full-length HMG-1 (100 ng/ml), or purified B box (10 µg/ml) for 18 hours. Following stimulation, cells were stained with a PE-labeled anti-CD25 monoclonal antibody and surface expression of CD25 was measured by flow cytometry. The results of this study are shown in FIG. 1B. Data are expressed as the ratio (fold-activation) of the percent of $CD25^+$ cells in unstimulated and stimulated cell populations that were gated to exclude the lowest 5% of cells based on mean FL1 fluorescence. In CHO/TLR2 cells, stimulation with each of HMGB1 and HMGB1 B box resulted in increased CD25 expression compared to the CHO/TLR4 samples.

Figure 1C:
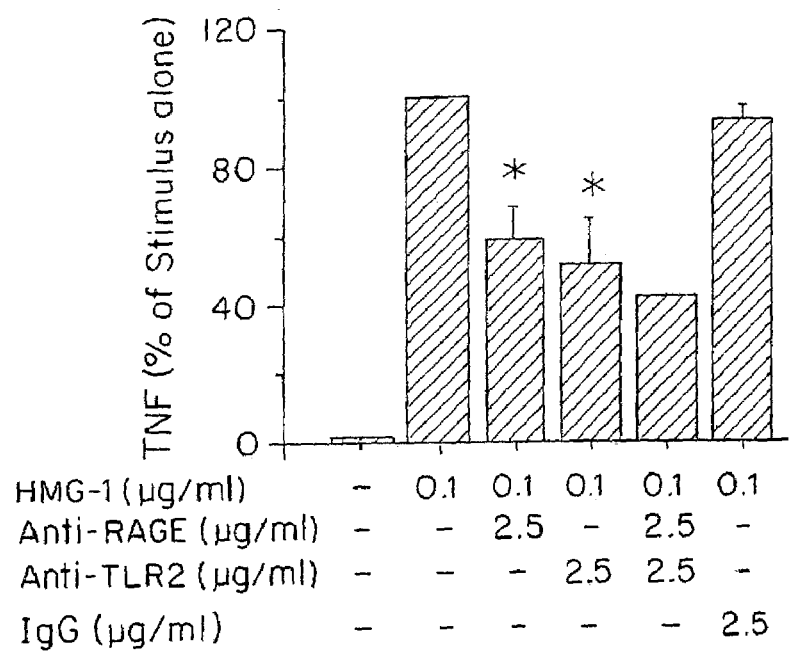
FIG. 1C is a histogram of the effect of administration of anti-RAGE antibody, anti-TLR2 antibody, anti-RAGE antibody and anti-TLR2 antibody together, or IgG on HMG1-mediated TNF release (measured as a percent of TNF release in the absence of antibody) in RAW 264.7 cells.

The effect of anti-RAGE antibodies, anti-TLR2 antibodies, a combination of anti-RAGE antibodies and anti-TLR2 antibodies or IgG, on HMG-1-mediated TNF release in RAW 264.7 cells was also determined. RAW 264.7 cells were seeded into 24-well tissue culture plates and used at 90% confluence. Cells were incubated with HMG-1 with or without anti-RAGE antibody (Cat# sc-8230, Santa Cruz Biotech Inc., Santa Cruz, Calif.), anti-TLR2 antibody (Affinity-purified polyclonal antibody, Cat # sc-12504, D17, Santa Cruz) or IgG (non-immune IgG, Sigma, St. Louis, Mo.) in Optimum I medium (Life Technologies, Grand Island, N.Y.) in the presence of polymyxin B (100 units/ml, Sigma, St. Louis, Mo.) for 16 hours. Antibodies were dialyzed against PBS to remove sodium azide before use. Conditioned media were collected and a TNF ELISA was performed, using standard ELISA methods. Data (n=3) were expressed as a percentage of the activity achieved with HMG-1 alone. The results of this study are shown in FIG. 1C. Both anti-RAGE and anti-TLR2 antibodies significantly (*P<0.05) inhibited HMG-1-mediated TNF release. Combination of the 2 antibodies had additive effects in inhibiting TNF release whereas IgG was irrelevant.

Toll-like receptor (TLR) proteins are highly conserved receptors that activate innate immune cells in response to a variety of endogenous and exogenous stimuli (Aderem and Ulevitch, Nature, 406:782–787 (2000)). To investigate whether HMGB1 signals through Toll-like receptors to release cytokine, macrophage-like RAW 264.7 cells stimulated with HMGB1 in the presence of anti-TLR2 antibody were used. Anti-TLR2 antibody caused approximately a 50% reduction in HMGB1-induced TNF release (Table 1), indicating that TLR2 participates in the inflammatory response of HMGB1.

TABLE 1

| Stimulus | TNF release (% compared to TNF release by HMGB1 alone) |
|---|---|
| HMGB1 (0.1 µg/ml) | 100% |
| HMGB1 (0.1 µg/ml) + anti-TLR2 (2.5 µg/ml) | 53 ± 13% |
| HMGB1 (0.1 µg/ml) + anti-RAGE (2.5 (µg/ml) | 58 ± 10% |
| HMGB1 (0.1 µg/ml) + anti-TLR2 + anti-RAGE (2.5 µg/ml each) | 48 ± 10% |
| HMGB1 (0.1 µg/ml) + IgG ((2.5 µg/ml) | 95 ± 6% |

To further examine the involvement of TLR2 in HMGB1 signaling, cultures of human embryonic kidney HEK cells stably transfected with fusion proteins consisting of CFP (cyan fluorescent protein) fused to either TLR2 or TLR4 at the C-terminus were used (provided by Drs. Douglas Golenbock and Eicke Latz, University of Massachusetts, School of Medicine, Boston, Mass.). The cell lines were cultured in in DMEM medium supplemented with 10% FBS, 1×penicillin/streptomycin, 1% L-glutamine, 500 µg/ml geneticin, and were used in experiments at 90% confluence. Experiments using these cell lines were performed under serum-free conditions.

Figures 2A, 2B:
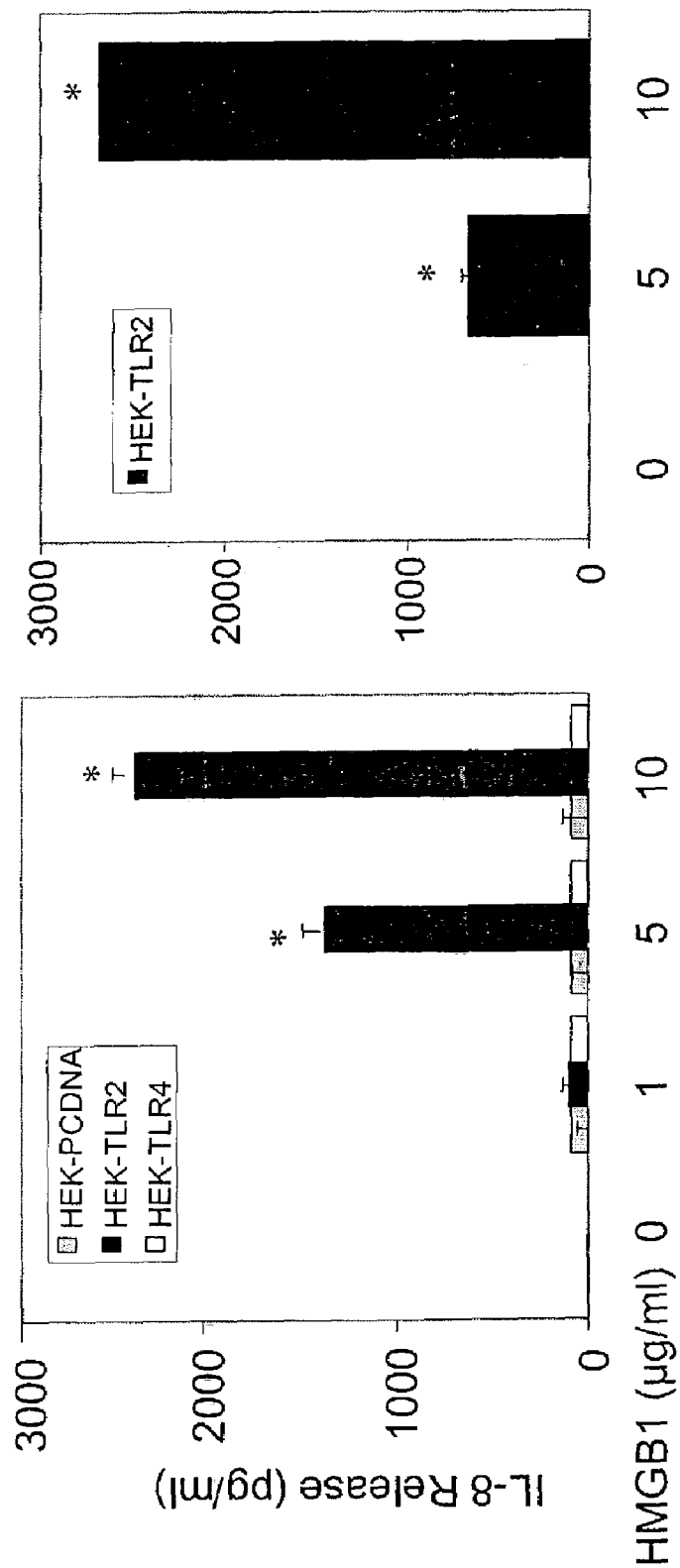
FIG. 2A is a histogram showing the effects of administration of HMGB1 (expressed in E. coli) to human embryonic kidney cells (HEK cells) stably transfected with pcDNA (HEK-PCDNA), TLR2 (HEK-TLR2), or TLR4 (HEK-TLR4). HEK cells over-expressing TLR2, TLR4, or vector alone (PC DNA) were plated in a 24-well culture plate and treated with HMGB1 (expressed in E. coli) at the concentrations indicated for 18 hours. IL-8 release in conditioned supernatants was measured by ELISA. Data shown are mean±SEM, n=3 or more.
FIG. 2B is a histogram showing the effects of administration of HMGB1 (expressed in Chinese hamster ovary (CHO) cells) to human embryonic kidney cells (HEK cells)

HMGB1 was produced in E. coli, as described by Wang et al. (Science, 285:248–251 (1999)). Briefly, a recombinant plasmid encoding rat HMGB1 was transformed into the protease-deficient E. coli strain BL21 (Novagen, Madison, Wis.) and grown in LB medium containing ampicillin (50 µg/ml), and fuision protein expression was induced by addition of 1 mM IPTG for 3 hours at 37° C. Bacteria were sonicated in ice-cold PBS plus 1×protease inhibitor cocktail and 1 mM PMSF. HMGB1 was purified with a calmodulin-binding resin column (Stratagene, La Jolla, Calif.) and passed over a polymyxin B column (Pierce, Rockford, Ill.) to remove possibly contaminating LPS. The integrity of protein was verified by SDS-PAGE with Coomassie Blue staining, with the purity predominantly over 85%. The HMGB1 protein was administered to the HEK-pcDNA (vector control), HEK-TLR2, and HEK-TLR4 cell lines at various concentrations, as indicated in FIG. 2A and release of IL-8 from the cells was measured using a commercially available ELISA kit from R&D Systems Inc. (Minneapolis, Minn.) according to the manufacturer's instructions. As shown in FIG. 2A, HMGB1 dose dependently stimulated IL-8 release in cells over-expressing TLR2 but not in cells over-expressing TLR4.

To ascertain that the effects of HMGB1 are not due to the possible minute amount of contaminants from bacteria, HMGB1 was expressed in mammalian CHO cells, to produce HMGB1 that was free of bacterial components. The CHO cell line was produced as follows. An N-terminal 3×Flag-tagged rat HMGB1 nucleic acid fragment was cloned into the plasmid pIRES2-EGFP (Clontech, Palo Alto, Calif.) to generate plasmid psF-HMGB1 using standard molecular biology techniques. A eukaryotic expression plasmid (psF-HMGB1) was engineered to secrete an N-terminal, 3×Flag-tagged rat HMGB1 recombinant protein. Plasmid psF-HMGB1 was transfected into CHO cells using the calcium phosphate method (Gibco-BRL, Grand Island, N.Y.) according to the manufacturer's instructions. Adherent CHO cells were grown in α-MEM media supplemented with 10% FBS and 2 mM glutamine. Transfected cells were selected for 10 days in 600 µg/ml active Geneticin. Stably transfected cells were FACS sorted for GFP (green fluorescent protein) expression and GFP-expressing cell lines were cloned by limiting dilution. A high HMGB1 secreting cell line (CHO HMGB1) was adapted to growth in suspension by using CHO-S-SFM II media supplemented with 300 µg/ml Geneticin and 1×penicillin/streptomycin. Fusion HMGB1 expression was about 0.5 µg/ml medium. HMGB1 protein was isolated from conditioned supernatant by affinity purification using flag antibody (ANTI-FLAG 2 affinity gel) according to the manufacturer's instructions (Sigma, St. Louis, Mo.).

The HMGB1 protein was administered to the HEK-TLR2 cell line at various doses, as indicated in FIG. 2B and release of IL-8 from the cells was measured using a commercially available ELISA kit from R&D Systems Inc. (Minneapolis, Minn.). As shown in FIG. 2B, recombinantly produced CHO cell derived HMGB1 stimulated IL-8 release from HEK-TLR2 cells. These results indicate that HMGB1 is an endogenous agonist of TLR2.

To ascertain the specificity of HMGB1 signaling, HEK-TLR2 cells were treated with nothing, HMGB1 alone, HMGB1 digested by trypsin, HMGB1 plus anti-HMGB1 antibody, HMGB1 plus IgG, or LPS alone, as indicated in FIG. 3A, and release of IL-8 from the cells was measured using a commercially available ELISA kit from R&D Systems Inc. (Minneapolis, Minn.). HMGB1 was trypsin-treated as follows. Trypsin-EDTA was added to purified HMGB1 (500 µg/ml in PBS) at 0.05% (final concentration), and digestion was carried out at 25° C. overnight. Proteins were visualized by Coomassie blue staining, and degradation of proteins was verified by SDS-PAGE before and after digestion. As shown in FIG. 3A, trypsin treatment of HMGB1 abolished HMGB1-induced IL-8 release, indicating that the effect of HMGB1 was specific. The anti-HMGB1 antibody significantly inhibited IL-8 release in cell cultures exposed to HMGB1. This data provides further evidence of the specificity of HMGB signaling. LPS, a known TLR4 agonist, stimulated IL-8 release in HEK-TLR4 cells administered LPS (FIG. 3B) but not in HEK-TLR2 cells, verifying that the transfected TLR proteins function similarly to endogenous TLR proteins in signal transduction. These results also show that residual amounts of LPS in HMGB preparations do not account for the observed effects of administration of HMGB to HEK-TLR2 cells.

TLR proteins transduce signals through an intermediate protein, MyD88 (Ombrellino et al., Lancer, 354:1446–1447 (2000)). To examine the possible role of MyD88 in mediating HMGB1 signaling, RAW 264.7 macrophages were co-transfected with plasmids encoding a dominant negative mutant MyD88 protein and an NF-κB-dependent luciferase reporter. The cells were then stimulated with HMGB1. The dominant negative MyD88 mutant significantly inhibited activation of NF-κB luciferase activity induced by HMGB1 (FIG. 4A). To address the specificity of the MyD88-dependent response, HMGB1 was added to cultures of CHO cells engineered to constitutively express either human TLR2 or TLR4 (FIG. 4B). These cells also contained an NF-κB-dependent CD25 reporter gene as previously described (Yoshimura et al., J. Immunol., 163: 1–5 (1999), and Delude et al., Journal of Immunology, 161:3001–3009 (1998)). HMGB1 failed to increase CD25 expression in TLR4-expressing cells, but significantly stimulated CD25 expression in CHO cells expressing TLR2, indicating that stimulation through TLR2 by HMGB1 is specific.

To further study whether HMGB1 signals via TLR2, macrophage-like RAW 264.7 cells were labeled with fluorescein isothiocyanate (FITC)-tagged HMGB1, produced using a commercially available kit (Pierce, Rockford, Ill.) according to the manufacturer's instructions. The labeling was carried out as follows. The cells were plated in 8-well slide chambers (Lab-Tek, Nalge Nunc Internationals, Naperville, Ill.) and used at 70% confluence. The cells were either left alone, or were pre-incubated in the presence of anti-TLR2 antibody or anti-TLR4 antibody (1 µg/ml) for 20 minutes at 37° C. in Opti-MEM I medium. FITC-labeled HMGB1 (1 µg/ml) was then added for an additional 15 minutes at 37° C. Cells were washed 3 times with PBS and fixed for 15 minutes at room temperature in 4% paraformaldehyde-PBS solution (pH 7.2). After fixing, cells were washed with PBS once and mounted for viewing by fluorescent confocal microscopy. Uptake of FITC-HMGB1 was observed in macrophages incubated with FITC-HMGB1 for 15 minutes at 37° C. (FIG. 5A). Pre-treatment with anti-TLR2 antibody markedly reduced the uptake as revealed by the decrease in cell-associated fluorescence (FIG. 5B). In contrast, pre-treatment with anti-TLR4 antibody did not have any effects on FITC-HMGB1 uptake (FIG. 5C) indicating that the effect of anti-TLR2 on blocking HMGB1 uptake was specific and thus further support that HMGB1 signals via TLR2.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for decreasing inflammation in an inflammatory condition selected from the group consisting of rheumatoid arthritis, systemic lupus erythematosus and allograft rejection in an individual comprising administering to said individual an effective amount of a soluble toll-like receptor 2 (sTLR2), wherein said sTLR2:
   comprises an amino acid sequence that has at least 95% sequence identity to amino acids 1-587 of SEQ ID NO:46;
   binds to a high mobility group box 1 (HMGB1) polypeptide; and
   inhibits HMGB1-mediated release of a proinflammatory cytokine from cells.

2. The method of claim 1, wherein said condition is rheumatoid arthritis.

3. The method of claim 1, wherein said condition is systemic lupus erythematosus.

4. The method of claim 1, wherein said condition is allograft rejection.

* * * * *

UNITED STATES PATENT AND TRADEMARK OFFICE
CERTIFICATE OF CORRECTION

| | | |
|---|---|---|
| PATENT NO. | : 7,220,723 B2 | |
| APPLICATION NO. | : 10/456947 | |
| DATED | : May 22, 2007 | |
| INVENTOR(S) | : Kevin J. Tracey et al. | |

It is certified that error appears in the above-identified patent and that said Letters Patent is hereby corrected as shown below:

In the specification, Column 1, line 8 through line 10,
Delete "The invention was supported, in whole or in part, by a grant GM 62508KT from the National Institutes of Health. The Government has certain rights in the invention."

and insert -- This invention was made with government support under grant GM 62508KT awarded by the National Institutes of Health. The government has certain rights in the invention. --

Signed and Sealed this
Twenty-ninth Day of March, 2011

David J. Kappos
*Director of the United States Patent and Trademark Office*